United States Patent
Doi et al.

(10) Patent No.: US 10,036,971 B2
(45) Date of Patent: Jul. 31, 2018

(54) CHARGING MEMBER, PROCESS CARTRIDGE, AND ELECTROPHOTOGRAPHIC IMAGE FORMING APPARATUS

(71) Applicant: CANON KABUSHIKI KAISHA, Tokyo (JP)

(72) Inventors: Noriyuki Doi, Numazu (JP); Kineo Takeno, Suntou-gun (JP); Noriko Suzumura, Mishima (JP); Hiroshi Mayuzumi, Yokohama (JP); Masataka Kodama, Mishima (JP); Kenichi Yamauchi, Mishima (JP); Hiroki Masu, Suntou-gun (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 372 days.

(21) Appl. No.: 14/721,734

(22) Filed: May 26, 2015

(65) Prior Publication Data
US 2015/0331348 A1  Nov. 19, 2015

Related U.S. Application Data

(63) Continuation of application No. PCT/JP2014/006472, filed on Dec. 25, 2014.

(30) Foreign Application Priority Data

Dec. 27, 2013  (JP) .................................. 2013-272398

(51) Int. Cl.
C07F 7/28  (2006.01)
C07F 7/00  (2006.01)
(Continued)

(52) U.S. Cl.
CPC ......... *G03G 15/0233* (2013.01); *C07F 5/069* (2013.01); *C07F 7/003* (2013.01); *C07F 7/28* (2013.01); *C07F 11/005* (2013.01)

(58) Field of Classification Search
CPC ... G03G 15/02; C07F 7/28; C07F 9/00; C07F 11/00
See application file for complete search history.

(56) References Cited

U.S. PATENT DOCUMENTS 8,192,910 B2  6/2012  Katoh et al.
8,383,234 B2  2/2013  Mayuzumi et al.
(Continued)

FOREIGN PATENT DOCUMENTS

CN  101625532 A  1/2010
CN  103097963 A  5/2013
(Continued)

*Primary Examiner* — Rip A Lee
(74) *Attorney, Agent, or Firm* — Fitzpatrick Cella Harper and Scinto

(57) ABSTRACT

Provided is a charging member that suppresses the occurrence of abnormal discharge under low temperature and low humidity. The charging member includes a support and a surface layer on the support, and the surface layer contains a compound represented by the following formula (a), (b), (c), or (d).

(a)

(b)

(Continued)

-continued

10 Claims, 4 Drawing Sheets

(51) Int. Cl.
*G03G 15/00* (2006.01)
*G03G 15/02* (2006.01)
*C07F 5/06* (2006.01)
*C07F 11/00* (2006.01)

(56) References Cited

U.S. PATENT DOCUMENTS

| | | |
|---|---|---|
| 8,440,307 B2 | 5/2013 | Nose et al. |
| 8,503,911 B2 | 8/2013 | Suzumura et al. |
| 8,526,857 B2 | 9/2013 | Tomomizu et al. |
| 8,548,359 B2 | 10/2013 | Taniguchi et al. |
| 2003/0104298 A1 | 6/2003 | Yamanaka et al. |
| 2009/0200572 A1* | 8/2009 | Kamamori ............ C09D 1/00 257/100 |
| 2010/0009282 A1 | 1/2010 | Katoh et al. |
| 2013/0004206 A1 | 1/2013 | Kuroda et al. |
| 2013/0034369 A1 | 2/2013 | Masu et al. |
| 2013/0064571 A1 | 3/2013 | Kodama et al. |
| 2013/0295330 A1 | 11/2013 | Kodama et al. |
| 2014/0072343 A1 | 3/2014 | Masu et al. |
| 2014/0080691 A1 | 3/2014 | Kurachi et al. |

FOREIGN PATENT DOCUMENTS

| | | | | |
|---|---|---|---|---|
| JP | 8-171262 A | * | 7/1996 | ............ G03G 15/02 |
| JP | 2000-26675 A | | 1/2000 | |
| JP | 2001-173641 A | | 6/2001 | |
| JP | 2002-173675 | * | 6/2002 | ............ C09K 11/08 |
| JP | 2002-173675 A | * | 6/2002 | ............ C09K 11/08 |
| JP | 2008-276025 A | | 11/2008 | |
| WO | 2013/175734 A1 | | 11/2013 | |

* cited by examiner

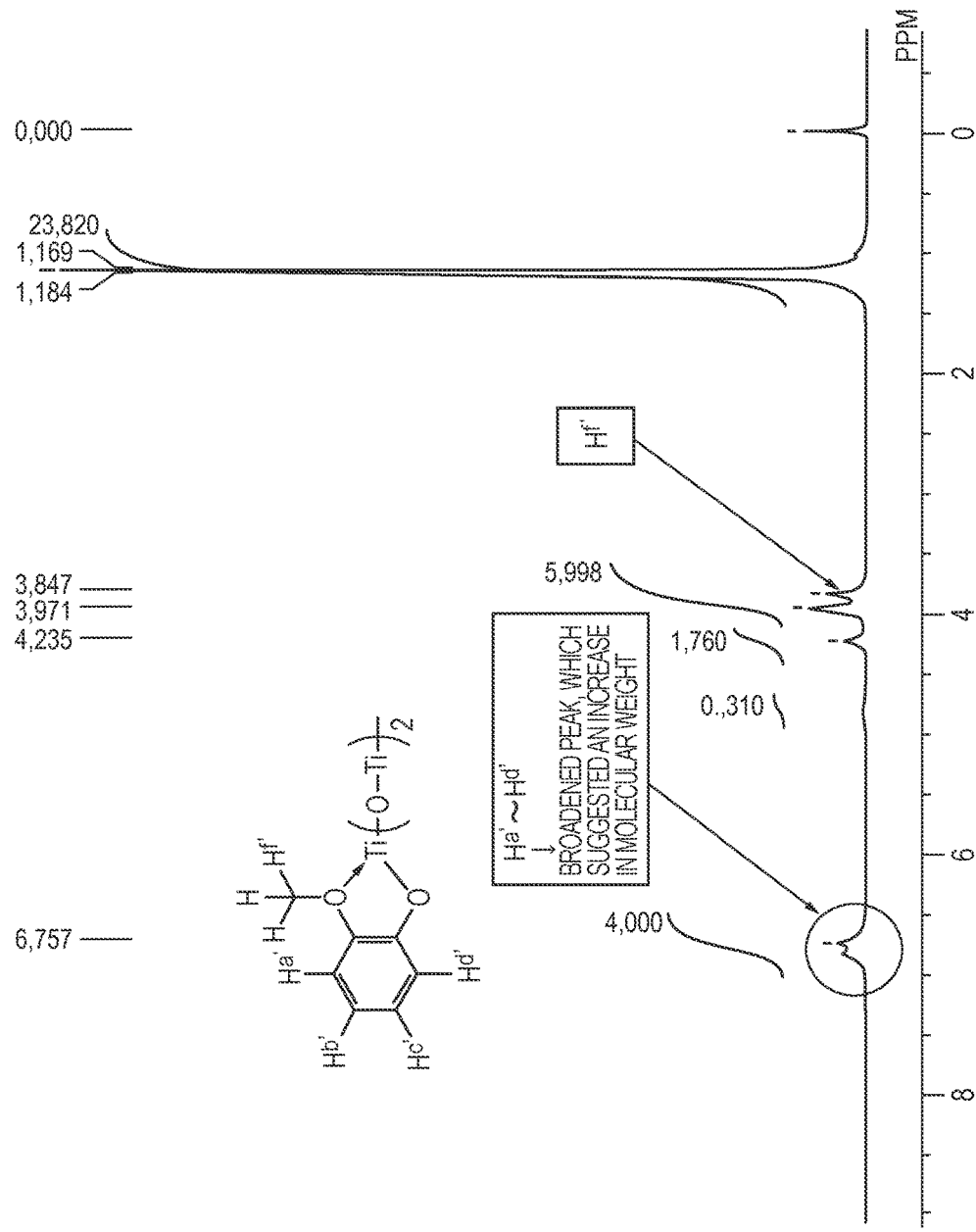

CHARGING MEMBER, PROCESS CARTRIDGE, AND ELECTROPHOTOGRAPHIC IMAGE FORMING APPARATUS

CROSS-REFERENCE TO RELATED APPLICATIONS

This application is a continuation of International Application No. PCT/JP2014/006472, filed Dec. 25, 2014, which claims the benefit of Japanese Patent Application No. 2013-272398, filed Dec. 27, 2013.

BACKGROUND OF THE INVENTION

Field of the Invention

The present invention relates to a charging member, and a process cartridge and an electrophotographic image forming apparatus (hereinafter referred to as "electrophotographic apparatus") each using the charging member.

Description of the Related Art

As one system for the charging of the surface of an electrophotographic photosensitive member (hereinafter referred to as "photosensitive member"), there is known a contact charging system. The contact charging system is a system involving applying a voltage to a charging member placed to be brought into contact with the photosensitive member to cause micro discharge near a contact portion between the charging member and the photosensitive member, thereby charging the surface of the photosensitive member.

The charging member to be used in the contact charging system generally includes a conductive elastic layer from the viewpoint of sufficiently securing a contact nip between the charging member and the photosensitive member. However, the conductive elastic layer contains a low-molecular weight component, and hence the low-molecular weight component bleeds out onto the surface of the charging member, with the result that an image defect may cause in some cases. Accordingly, a surface layer is provided on the conductive elastic layer in some cases for the purpose of suppressing the bleeding out of the low-molecular weight component onto the surface of the charging member.

Japanese Patent Application Laid-Open No. 2001-173641 proposes that the surface of a conductive roll base material be covered with an inorganic oxide film formed by a sol-gel method.

SUMMARY OF THE INVENTION

In recent years, the time period for which a photosensitive member is charged has been relatively shortening in association with an increase in speed of an electrophotographic image forming process, which is disadvantageous for stable and reliable charging of the photosensitive member.

Investigations made by the inventors of the present invention have found that when the conductive roll according to Japanese Patent Application Laid-Open No. 2001-173641 is used as a charging member, in association with an increase in process speed, local and strong discharge (abnormal discharge) may occur particularly under low temperature and low humidity. In addition, the investigations have found that an uneven image of from about several tens of micrometers to several millimeters resulting from the abnormal discharge may occur.

The present invention is directed to providing a charging member having an excellent charging performance, the charging member being capable of suppressing the occurrence of local and strong discharge (abnormal discharge) even under low temperature and low humidity. Also, the present invention is directed to providing a process cartridge and an electrophotographic apparatus each of which can suppress the occurrence of local and strong discharge (abnormal discharge) even under low temperature and low humidity, and can form a high-quality electrophotographic image.

According to one aspect of the present invention, there is provided a charging member, including: a support; and a surface layer on the support, in which the surface layer contains a compound represented by the following formula (a).

(a)

In the formula (a), L1 represents a polymetalloxane having a structural unit represented by $M1O_{n/2}$. n represents an integer of 1 or more and p or less when a valence of a metal atom M1 is p. M1 represents at least one metal atom selected from the group consisting of Ti, Zr, Hf, V, Nb, Ta, W, Al, Ga, In, and Ge.

X1 represents any one of structures represented by the following formulae (1) to (4).

(1)

(2)

(3)

(4)

In the formulae (1) to (4), * represents a bonding site with A1 and ** represents a bonding site with M1 in L1.

Y1 represents a group having a site that coordinates to M1 in L1.

(i) When X1 represents a structure represented by the formula (1), A1 represents an atomic group needed for forming a four- to eight-membered ring together with M1, X1, and Y1, the atomic group containing an aromatic ring, and one constituent carbon atom of the aromatic ring is bonded to an oxygen atom of X1, and (ii) when X1 represents a structure represented by any one of the formulae (2) to (4), A1 represents a bond or atomic group needed for forming a four- to eight-membered ring together with M1, X1, and Y1.

According to another aspect of the present invention, there is provided a charging member, including: a support; and a surface layer on the support, in which the surface layer contains a compound represented by the following formula (b).

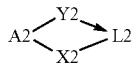
(b)

In the formula (b), L2 represents a metal alkoxide or metal hydroxide having a metal atom M2. M2 represents at least one metal atom selected from the group consisting of Ti, Zr, Hf, V, Nb, Ta, W, Al, Ga, In, and Ge.

X2 represents any one of structures represented by the following formulae (5) to (8).

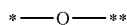 (5)

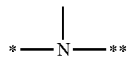 (6)

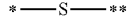 (7)

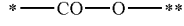 (8)

In the formulae (5) to (8), * represents a bonding site with A2 and ** represents a bonding site with M2 in L2.

Y2 represents a group having a site that coordinates to M2 in L2.

(i) When X2 represents a structure represented by the formula (5), A2 represents an atomic group needed for forming a four- to eight-membered ring together with M2, X2, and Y2, the atomic group containing an aromatic ring, and one constituent carbon atom of the aromatic ring is bonded to an oxygen atom of X2, and (ii) when X2 represents a structure represented by any one of the formulae (6) to (8), A2 represents a bond or atomic group needed for forming a four- to eight-membered ring together with M2, X2, and Y2.

According to still another aspect of the present invention, there is provided a charging member, including: a support; and a surface layer on the support, in which the surface layer contains at least one of compounds represented by the following formulae (c) and (d).

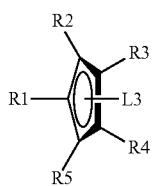 (c)

In the formula (c), L3 represents a polymetalloxane having a structural unit represented by $M3O_{m/2}$. M3 represents at least one metal atom selected from the group consisting of Ti, Zr, Hf, V, Nb, Ta, W, Al, Ga, In, and Ge. m represents an integer of 1 or more and q or less when a valence of a metal atom M3 is q. R1 to R5 each independently represent a hydrogen atom, an alkyl group having 1 to 4 carbon atoms, or a trimethylsilyl group. A cyclopentadienyl group coordinates to the metal atom M3 in L3.

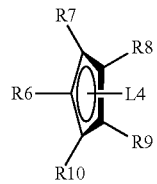 (d)

In the formula (d), L4 represents a metal alkoxide or metal hydroxide having a metal atom M4. M4 represents at least one metal atom selected from the group consisting of Ti, Zr, Hf, V, Nb, Ta, W, Al, Ga, In, and Ge. R6 to R10 each independently represent a hydrogen atom, an alkyl group having 1 to 4 carbon atoms, or a trimethylsilyl group. A cyclopentadienyl group coordinates to the metal atom M4 in L4.

According to yet still another aspect of the present invention, there is provided a process cartridge, including: a photosensitive member; and a charging member placed to be capable of charging a surface of the photosensitive member, the process cartridge being removably mounted onto a main body of an electrophotographic apparatus, in which the charging member includes the above-mentioned charging member. According to yet still another aspect of the present invention, there is provided an electrophotographic apparatus, including: a photosensitive member; and a charging member placed to be capable of charging a surface of the photosensitive member, in which the charging member includes the above-mentioned charging member.

According to the present invention, it is possible to provide the charging member having an excellent charging performance, the charging member being capable of suppressing the occurrence of local and strong discharge (abnormal discharge) even under low temperature and low humidity. According to the other embodiments of the present invention, it is possible to provide the process cartridge and the electrophotographic apparatus each of which can suppress the occurrence of local and strong discharge (abnormal discharge) even under low temperature and low humidity, and can form a high-quality electrophotographic image.

Further features of the present invention will become apparent from the following description of exemplary embodiments with reference to the attached drawings.

BRIEF DESCRIPTION OF THE DRAWINGS

FIG. 5 shows the results of the $^1$H-NMR spectral analysis of an example of the compound contained in the surface layer of the present invention.

DESCRIPTION OF THE EMBODIMENTS

Figure 1:
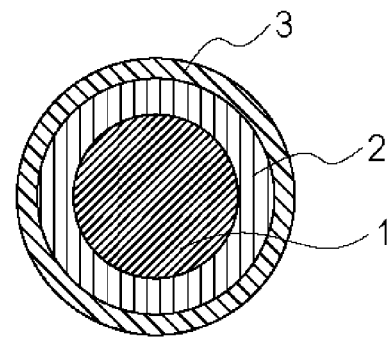
FIG. 1 is a sectional view of an example of a charging member of the present invention.

Preferred embodiments of the present invention will now be described in detail in accordance with the accompanying drawings.

Details about compounds and structures represented by the following formulae (a) to (f) according to the present invention are described below.

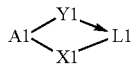
(a)

In the formula (a), L1 represents a polymetalloxane having a structural unit represented by $M1O_{n/2}$. n represents an integer of 1 or more and p or less when the valence of a metal atom M1 is p. M1 represents at least one metal atom selected from the group consisting of Ti, Zr, Hf, V, Nb, Ta, W, Al, Ga, In, and Ge.

X1 represents any one of structures represented by the following formulae (1) to (4).

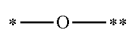
(1)

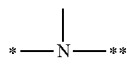
(2)

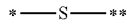
(3)

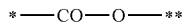
(4)

In the formulae (1) to (4), * represents a bonding site with A1 and ** represents a bonding site with M1 in L1.

Y1 represents a group having a site that coordinates to M1 in L1.

(i) When X1 represents a structure represented by the formula (1), A1 represents an atomic group needed for forming a four- to eight-membered ring together with M1, X1, and Y1, the atomic group containing an aromatic ring, and one constituent carbon atom of the aromatic ring is bonded to an oxygen atom of X1, and (ii) when X1 represents a structure represented by any one of the formulae (2) to (4), A1 represents a bond or atomic group needed for forming a four- to eight-membered ring together with M1, X1, and Y1.

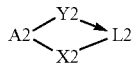
(b)

In the formula (b), L2 represents a metal alkoxide or metal hydroxide having a metal atom M2. M2 represents at least one metal atom selected from the group consisting of Ti, Zr, Hf, V, Nb, Ta, W, Al, Ga, In, and Ge.

X2 represents any one of structures represented by the following formulae (5) to (8).

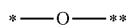
(5)

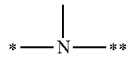
(6)

(7)

(8)

In the formulae (5) to (8), * represents a bonding site with A2 and ** represents a bonding site with M2 in L2.

Y2 represents a group having a site that coordinates to M2 in L2.

(i) When X2 represents a structure represented by the formula (5), A2 represents an atomic group needed for forming a four- to eight-membered ring together with M2, X2, and Y2, the atomic group containing an aromatic ring, and one constituent carbon atom of the aromatic ring is bonded to an oxygen atom of X2, and (ii) when X2 represents a structure represented by any one of the formulae (6) to (8), A2 represents a bond or atomic group needed for forming a four- to eight-membered ring together with M2, X2, and Y2.

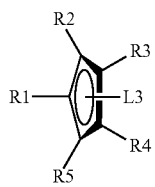
(c)

In the formula (c), L3 represents a polymetalloxane having a structural unit represented by $M3O_{m/2}$. M3 represents at least one metal atom selected from the group consisting of Ti, Zr, Hf, V, Nb, Ta, W, Al, Ga, In, and Ge. m represents an integer of 1 or more and q or less when the valence of a metal atom M3 is q. R1 to R5 each independently represent a hydrogen atom, an alkyl group having 1 to 4 carbon atoms, or a trimethylsilyl group. A cyclopentadienyl group coordinates to the metal atom M3 in L3.

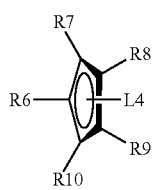
(d)

In the formula (d), L4 represents a metal alkoxide or metal hydroxide having a metal atom M4. M4 represents at least one metal atom selected from the group consisting of Ti, Zr, Hf, V, Nb, Ta, W, Al, Ga, In, and Ge. R6 to R10 each independently represent a hydrogen atom, an alkyl group having 1 to 4 carbon atoms, or a trimethylsilyl group. A cyclopentadienyl group coordinates to the metal atom M4 in L4.

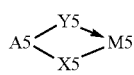
(e)

In the formula (e), X5 represents any one of structures represented by the following formulae (12) to (15).

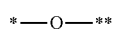
(12)

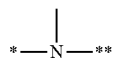
(13)

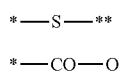
(14)

(15)

In the formulae (12) to (15), * represents a bonding site with A5 and ** represents a bonding site with M5.

Y5 represents a group having a site that coordinates to M5.

(i) When X5 represents a structure represented by the formula (12), A5 represents an atomic group needed for forming a four- to eight-membered ring together with M5, X5, and Y5, the atomic group containing an aromatic ring, and one constituent carbon atom of the aromatic ring is bonded to an oxygen atom of X5, and (ii) when X5 represents a structure represented by any one of the formulae (13) to (15), A5 represents a bond or atomic group needed for forming a four- to eight-membered ring together with M5, X5, and Y5.

(f)

In the formula (f), R61 to R65 each independently represent a hydrogen atom, an alkyl group having 1 to 4 carbon atoms, or a trimethylsilyl group, and a cyclopentadienyl group coordinates to M6.

That is, the surface layer of a charging member according to the present invention has a feature of containing such a compound that a compound having a specific structure coordinates and bonds to a metal atom in a polymetalloxane structure, metal alkoxide, or metal hydroxide.

In addition, the reason why the charging member according to the present invention can suppress the occurrence of abnormal discharge is considered to be as described below.

A proximity discharge phenomenon in the air occurs in accordance with Paschen's law. The phenomenon is the diffusion phenomenon of an electron avalanche in which the following process is repeated: free electrons are accelerated by an electric field and collide with molecules present between electrodes or with the electrodes to produce an electron, a cation, and an anion. The electron avalanche diffuses in accordance with the electric field and the diffusion determines the final discharge charge quantity. When the electric field becomes excessive as compared with a condition following Paschen's law, local and strong discharge, i.e., abnormal discharge is liable to occur.

Under low temperature and low humidity, the number of molecules present between the electrodes is smaller than that under normal temperature and normal humidity, and hence a discharge start voltage tends to be higher than a discharge start voltage derived from Paschen's law. When the discharge start voltage increases, the electric field is liable to be excessive as compared with the condition following Paschen's law, and hence the abnormal discharge is liable to occur under low temperature and low humidity.

In the compound according to the present invention, a ligand having a specific structure coordinates and bonds to the metal atom in the polymetalloxane, metal alkoxide, or metal hydroxide. Accordingly, the energy level of its highest occupied molecular orbital (HOMO) becomes shallower than that before the coordination of the ligand. As a result, an electron is easily discharged from the surface layer of the charging member according to the present invention. Accordingly, the discharge start voltage reduces and the discharge charge quantity is suppressed, and hence the occurrence of the abnormal discharge may be suppressed.

<Charging Member>

Hereinafter, the present invention is described in detail by taking a roller-shaped charging member (hereinafter sometimes referred to as "charging roller") as a specific example of the charging member of the present invention. The shape of the charging member is not limited to a roller shape and any shape is permitted.

FIG. 1 illustrates a charging roller having an elastic layer 2 and surface layer 3 formed on a support 1.

A construction having an elastic layer is preferably used for a charging member placed to be capable of charging the surface of an electrophotographic photosensitive member (hereinafter sometimes referred to as "photosensitive member") in order that a contact nip between the charging member and the photosensitive member may be sufficiently secured. The simplest construction of the charging member having the elastic layer is a construction in which two layers, i.e., the elastic layer and a surface layer are provided on a support. One or two or more other layers may be provided between the support and the elastic layer or between the elastic layer and the surface layer.

[Surface Layer]

Hereinafter, the compounds represented by the formulae (a), (b), (c), and (d), and the polymetalloxanes having structures represented by the formulae (e) and (f) are described in detail.

<Compound Represented by Formula (a) or (b)>

L1 in the formula (a) represents a polymetalloxane having a structural unit represented by $M1O_{n/2}$. M1 represents at least one metal atom selected from the group consisting of Ti, Zr, Hf, V, Nb, Ta, W, Al, Ga, In, and Ge, and n represents an integer of 1 or more and p or less when the valence of a metal atom M1 is p. The metal atom M1 in the polymetalloxane may be a plurality of kinds of metal atoms. In addition, the polymetalloxane may have a structural unit represented by $SiO_{r/2}$ (r represents an integer of 1 or more and 4 or less). When the polymetalloxane has the structural unit, the amorphous property of the polymetalloxane improves, and hence the smoothness and strength of a film can be additionally improved.

L2 in the formula (b) represents a metal alkoxide or metal hydroxide having a metal atom M2. The metal atom M2 represents at least one metal atom selected from the group consisting of Ti, Zr, Hf, V, Nb, Ta, W, Al, Ga, In, and Ge.

X1 in the formula (a) represents any one of the structures represented by the following formulae (1) to (4).

(1)

(2)

(3)

(4)

In the formulae (1) to (4), * represents a bonding site with A1 and ** represents a bonding site with M1 in L1.

X2 in the formula (b) represents any one of the structures represented by the following formulae (5) to (8).

*—O—** (5)

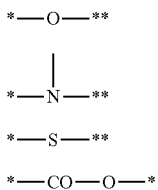
(6)

*—S—** (7)

*—CO—O—** (8)

In the formulae (5) to (8), * represents a bonding site with A2 and ** represents a bonding site with M2 in L2.

In the formulae (2) and (6), the nitrogen atom may be a nitrogen atom in a heterocycle such as a pyrrole skeleton, an indole skeleton, a pyrrolidine skeleton, a carbazole skeleton, an imidazole skeleton, a benzimidazole skeleton, a pyrazole skeleton, an indazole skeleton, a triazole skeleton, a benzotriazole skeleton, a tetrazole skeleton, a pyrrolidone skeleton, a piperidine skeleton, a morpholine skeleton, or a piperazine skeleton, each of which may be substituted or unsubstituted. An example of the substituent is a linear or branched alkyl group or alkoxy group having 1 to 10 carbon atoms. The number of carbon atoms is more preferably from 1 to 4 (unless otherwise stated, a substituent that appears hereinafter is the same as the substituent described here). When the nitrogen atom is not a nitrogen atom in a heterocycle, the atom or group except A1 and M1 to which the nitrogen atom is bonded, and the atom or group except A2 and M2 to which the nitrogen atom is bonded each represent a hydrogen atom, a substituted or unsubstituted aryl group, or an alkyl group having 1 to 10 carbon atoms. Specific examples thereof include: aryl groups such as a phenyl group and a naphthyl group; linear alkyl groups such as a methyl group, an ethyl group, a n-propyl group, a n-butyl group, a n-hexyl group, a n-octyl group, and a n-decyl group; alkyl groups each having a branched chain such as an isopropyl group and a t-butyl group; and cyclic alkyl groups such as a cyclopentyl group and a cyclohexyl group. In particular, the groups represented by the formulae (2) and (6) are each desirably a group obtained by removing one hydrogen atom bonded to a nitrogen atom from an unsubstituted amino group, a monoalkylamino group having 1 to 4 carbon atoms, or a group having a pyrrole skeleton.

Y1 in the formula (a) represents a group having a site that coordinates to M1 in L1, and Y2 in the formula (b) represents a group having a site that coordinates to M2 in L2 and the group contains an atom having an unshared electron pair. Specific examples thereof include a hydroxy group, an alkoxy group, an aryloxy group, a carbonyl group, an alkylthio group, an arylthio group, a thiocarbonyl group, a substituted or unsubstituted amino group, and a substituted or unsubstituted imino group.

An example of the alkoxy group is a linear or branched alkoxy group having 1 to 10 carbon atoms. Specific examples thereof include a methoxy group, an ethoxy group, a n-propoxy group, an iso-propoxy group, a n-butoxy group, and a t-butoxy group. Preferably, the alkoxy group is an alkoxy group having 1 to 4 carbon atoms.

Examples of the aryloxy group include a substituted or unsubstituted phenoxy group and a substituted or unsubstituted naphtyloxy group.

An example of the alkylthio group is a group obtained by replacing an oxygen atom in an alkoxy group with a sulfur atom.

An example of the arylthio group is a group obtained by replacing an oxygen atom in an aryloxy group with a sulfur atom.

Examples of the carbonyl group include a formyl group, an alkylcarbonyl group, an alkoxycarbonyl group, an arylcarbonyl group, an amide group (R—CO—NR— or R—NR—CO—), a ureido group ($NH_2$—CO—NH—), and a urea group (R—NH—CO—NH—). Each of the alkyl group in the alkylcarbonyl group and the alkoxycarbonyl group, and R in the amide group and the urea group is preferably a linear or branched alkyl group having 1 to 10 carbon atoms. Specific examples thereof include: linear alkyl groups such as a methyl group, an ethyl group, a n-propyl group, a n-butyl group, a n-hexyl group, a n-octyl group, a n-nonyl group, and a n-decyl group; and branched alkyl groups such as an isopropyl group and a t-butyl group. The number of carbon atoms is more preferably from 1 to 4.

Examples of the arylcarbonyl group include a group in which a carbonyl group is bonded to a substituted or unsubstituted aromatic hydrocarbon, and a group in which a carbonyl group is bonded to a substituted or unsubstituted aromatic heterocycle. Specific examples thereof include a substituted or unsubstituted phenylcarbonyl group and a substituted or unsubstituted naphtylcarbonyl group.

Examples of the thiocarbonyl group include a group obtained by replacing an oxygen atom in the carbonyl group with a sulfur atom.

Examples of the substituted amino group include an alkylamino group, a dialkylamino group, and a substituted or unsubstituted arylamino group. Specific examples thereof include: monoalkylamino groups each having 1 to 10 carbon atoms such as a monomethylamino group and a monoethylamino group; dialkylamino groups each having 1 to 10 carbon atoms such as a dimethylamino group, a diethylamino group, and an ethylmethylamino group; and substituted or unsubstituted arylamino groups such as a monophenylamino group, a methylphenylamino group, a diphenylamino group, and a naphthylamino group.

The unsubstituted imino group is a group represented by >C=NH or —N=$CH_2$. A hydrogen atom in the unsubstituted imino group may be substituted with an alkyl group having 1 to 10 carbon atoms, or a substituted or unsubstituted aryl group (a phenyl group, a naphthyl group).

Further, Y1 and Y2 may each represent a group having an aliphatic or aromatic heterocyclic skeleton. Examples of the aromatic heterocyclic skeleton include a thiophene skeleton, a furan skeleton, a pyridine skeleton, a pyran skeleton, a benzothiophene skeleton, a benzofuran skeleton, a quinoline skeleton, an isoquinoline skeleton, an oxazole skeleton, a benzoxazole skeleton, a triazole skeleton, a benzothiazole skeleton, a thiadiazole skeleton, a benzothiadiazole skeleton, a pyridazine skeleton, a pyrimidine skeleton, a pyrazine skeleton, a phenazine skeleton, an acridine skeleton, a xanthene skeleton, an imidazole skeleton, a benzimidazole skeleton, a pyrazole skeleton, an indazole skeleton, a triazole skeleton, a benzotriazole skeleton, and a tetrazole skeleton, each of which may be substituted or unsubstituted. An example of the aliphatic heterocyclic skeleton is a substituted or unsubstituted morpholine skeleton.

Of the above-mentioned groups, Y1 and Y2 each preferably represent a hydroxy group, an alkoxy group having 1 to 4 carbon atoms, a substituted or unsubstituted phenoxy group, a substituted or unsubstituted naphthyloxy group, a formyl group, an alkylcarbonyl group having an alkyl group having 1 to 4 carbon atoms, an alkoxycarbonyl group having an alkoxy group having 1 to 4 carbon atoms, a thiocarbonyl group, a dimethylamide group, a diethylamide group, an ethylmethylamide group, an unsubstituted amino group, a monomethylamino group, a monoethylamino group, a dimethylamino group, a diethylamino group, a monophenylamino group, a methylethylamino group, a methylphenylamino group, a diphenylamino group, a naphthylamino group, an unsubstituted imino group, a methylimino group, an ethylimino group, a group having a pyridine skeleton, a group having a quinoline skeleton, or a group having an isoquinoline skeleton.

When X1 represents a structure represented by the formula (1), A1 in the formula (a) represents an atomic group needed for forming a four- to eight-membered ring together with M1, X1, and Y1, the atomic group containing an aromatic ring, and one constituent carbon atom of the aromatic ring is bonded to the oxygen atom of X1. Similarly, when X2 represents a structure represented by the formula (5), A2 in the formula (b) represents an atomic group needed for forming a four- to eight-membered ring together with M2, X2, and Y2, the atomic group containing an aromatic ring, and one constituent carbon atom of the aromatic ring is bonded to the oxygen atom of X2.

Specific examples of A1 and A2 include atomic groups each containing a substituted or unsubstituted aromatic ring (a benzene ring, a naphthalene ring, a pyrrole ring, a thiophene ring, a furan ring, a pyridine ring, an indole ring, a benzothiophene ring, a benzofuran ring, a quinoline ring, an isoquinoline ring, or the like). In addition, A1 and A2 may form fused rings together with the aromatic heterocycles of Y1 and Y2, respectively. A1 and A2 each particularly preferably represent an atomic group containing an aromatic ring (a benzene ring or a naphthalene ring).

It should be noted that it is important for each of A1 when X1 represents a structure represented by the formula (1) and A2 when X2 represents a structure represented by the formula (5) to have an aromatic ring. When A1 and A2 each have an aromatic ring, a metal complex having a structure formed by A1, M1, X1, and Y1, and a metal complex having a structure formed by A2, M2, X2, and Y2 each have high stability, and the performance stability of the charging member is also high.

When X1 represents any one of the structures represented by the formulae (2) to (4), A1 in the formula (a) represents a bond or atomic group needed for forming a four- to eight-membered ring together with M1, X1, and Y1. Similarly, when X2 represents a structure represented by any one of the formulae (6) to (8), A2 in the formula (b) represents a bond or atomic group needed for forming a four- to eight-membered ring together with M2, X2, and Y2. When A2 (A1) represents an atomic group needed for forming a four- to eight-membered ring together with M2 (M1), X2 (X1), and Y2 (Y1), examples of the atomic group include the following: alkylene groups such as a methylene group and an ethylene group; and atomic groups each containing an aromatic ring (a benzene ring, a naphthalene ring, a pyrrole ring, a thiophene ring, a furan ring, a pyridine ring, an indole ring, a benzothiophene ring, a benzofuran ring, a quinoline ring, and isoquinoline ring).

A1 and A2 each particularly preferably represent a bond, an alkylene group, or an atomic group containing an aromatic ring (a benzene ring, a naphthalene ring).

In addition, when A1 and A2 each represent an atomic group containing an aromatic ring, A1 and A2 may form fused rings together with the aromatic heterocycles of Y1 and Y2 or the aromatic heterocycles of X1 and X2, or both of such aromatic heterocycles, respectively.

In the formulae (a) and (b), a ring formed by A1, M1, X1, and Y1, and a ring formed by A2, M2, X2, and Y2 are each preferably a five- or six-membered ring from the viewpoint of the ease with which a complex is formed.

Two preferred combinations of A1, X1, and Y1 in the formula (a) are given below.

A1 represents a structure represented by the following formula (A1-1) or (A1-2), X1 represents a structure represented by the following formula (X1-1) or (X1-2), and Y1 represents a methoxy group, an ethoxy group, a formyl group, a methylcarbonyl group, an ethylcarbonyl group, a methoxycarbonyl group, an ethoxycarbonyl group, a dimethylamide group, a diethylamide group, a methylethylamide group, a methylthio group, an ethylthio group, a thiocarbonyl group, a dimethylamino group, a diethylamino group, an ethylmethylamino group, an unsubstituted imino group, a methylimino group, an ethylimino group, a group having a pyridine skeleton, a group having a quinoline skeleton, or a group having an isoquinoline skeleton.

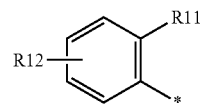

(A1-1)

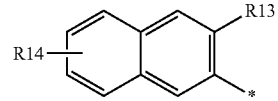

(A1-2)

(In the formulae (A1-1) and (A1-2), R11 and R13 each represent a single bond or methylene group bonded to Y1, R12 and R14 each represent a hydrogen atom, a methoxy group, or an ethoxy group, and * represents a bonding site with X1.)

*—O—**           (X1-1)

*—CO—O—**        (X1-2)

(In the formulae (X1-1) and (X1-2), * represents a bonding site with A1 and ** represents a bonding site with M1.)

It should be noted that in the above-mentioned combination, the case where Y1 represents a group having a pyridine skeleton, a group having a quinoline skeleton, or a group having an isoquinoline skeleton includes a fused ring formed of an aromatic ring in Y1 and an aromatic ring in A1 as well.

Further, A1 represents a bond, a methylene group, an ethylene group, or a trimethylene group, X1 represents a structure represented by any one of the following formulae (X1-3) to (X1-7), and Y1 represents a methoxy group, an ethoxy group, a formyl group, a methylcarbonyl group, an ethylcarbonyl group, a methoxycarbonyl group, an ethoxycarbonyl group, a dimethylamide group, a diethylamide group, a methylethylamide group, a methylthio group, an ethylthio group, a thiocarbonyl group, a dimethylamino group, a diethylamino group, an ethylmethylamino group, an unsubstituted imino group, a methylimino group, an ethylimino group, a group having a pyridine skeleton, a group having a quinoline skeleton, or a group having an isoquinoline skeleton.

*—NCH$_3$—**        (X1-3)

*—NH—**           (X1-4)

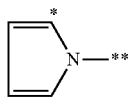 (X1-5)

*—S—** (X1-6)

*—CO—O—** (X1-7)

(In the formulae (X1-3) and (X1-7), * represents a bonding site with A1 and ** represents a bonding site with M1.)

It should be noted that in the two combinations of A1, X1, and Y1, the ring formed by A1, M1, X1, and Y1 is more preferably a five- or six-membered ring from the viewpoint of the ease with which a complex is formed.

In addition, two preferred combinations of A2, X2, and Y2 in the formula (b) are given below.

A2 represents a structure represented by the following formula (A2-1) or (A2-2), X2 represents a structure represented by the following formula (X2-1) or (X2-2), and Y2 represents a methoxy group, an ethoxy group, a formyl group, a methylcarbonyl group, an ethylcarbonyl group, a methoxycarbonyl group, an ethoxycarbonyl group, a dimethylamide group, a diethylamide group, a methylethylamide group, a methylthio group, an ethylthio group, a thiocarbonyl group, a dimethylamino group, a diethylamino group, an ethylmethylamino group, an unsubstituted imino group, a methylimino group, an ethylimino group, a group having a pyridine skeleton, a group having a quinoline skeleton, or a group having an isoquinoline skeleton.

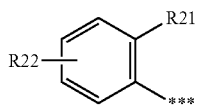 (A2-1)

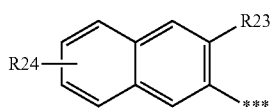 (A2-2)

(In the formulae (A2-1) and (A2-2), R21 and R23 each represent a single bond or methylene group bonded to Y2, R22 and R24 each represent a hydrogen atom, a methoxy group, or an ethoxy group, and *** represents a bonding site with X2.)

*—O—** (X2-1)

*—CO—O—** (X2-2)

(In the formulae (X2-1) and (X2-2), * represents a bonding site with A2 and ** represents a bonding site with M2.)

It should be noted that in the above-mentioned combination, the case where Y2 represents a group having a pyridine skeleton, a group having a quinoline skeleton, or a group having an isoquinoline skeleton includes a fused ring formed of an aromatic ring in Y2 and an aromatic ring in A2 as well.

Further, A2 represents a bond, a methylene group, an ethylene group, or a trimethylene group, X2 represents a structure represented by any one of the following formulae (X2-3) to (X2-7), and Y2 represents a methoxy group, an ethoxy group, a formyl group, a methylcarbonyl group, an ethylcarbonyl group, a methoxycarbonyl group, an ethoxycarbonyl group, a dimethylamide group, a diethylamide group, a methylethylamide group, a methylthio group, an ethylthio group, a thiocarbonyl group, a dimethylamino group, a diethylamino group, an ethylmethylamino group, an unsubstituted imino group, a methylimino group, an ethylimino group, a group having a pyridine skeleton, a group having a quinoline skeleton, or a group having an isoquinoline skeleton.

*—NCH$_3$—** (X2-3)

*—NH—** (X2-4)

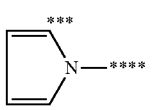 (X2-5)

*—S—** (X2-6)

*—CO—O—** (X2-7)

(In the formulae (X2-3) to (X2-7), * represents a bonding site with A2 and ** represents a bonding site with M2.)

It should be noted that in the two combinations of A2, X2, and Y2, the ring formed by A2, M2, X2, and Y2 is more preferably a five- or six-membered ring from the viewpoint of the ease with which a complex is formed.

With regard to the formulae (a) and (b), specific examples of the compound that coordinates and bonds to a metal atom to form such structure as described above (hereinafter sometimes referred to as "compound for a ligand") are collectively shown in Tables 1 to 4. It should be noted that in Tables 1 to 4, the symbol "Me" means a methyl group.

Some of the compounds for ligands shown in Tables 1 to 4 are taken and described in detail.

An example of the compound for a ligand in each of the case where X1 represents a structure represented by the formula (1) and the case where X2 represents a structure represented by the formula (5) is guaiacol represented by the formula (9).

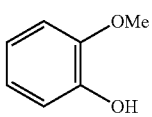 (9)

As shown in Example 1 in Table 10, guaiacol forms a complex as follows: the hydrogen atom of its hydroxy group removes and the remaining oxygen atom bonds to a metal atom, and the oxygen atom of its methoxy group undergoes coordination bonding with the metal atom. The remaining 1,2-phenylene group corresponds to each of A1 and A2.

Another example of the compound for a ligand in each of the case where X1 represents a structure represented by the formula (1) and the case where X2 represents a structure represented by the formula (5) is 4-hydroxy-5-azaphenanthrene represented by the following formula (10). 4-Hydroxy-5-azaphenanthrene is such a compound for a ligand that aromatic rings in A1 and A2 are integrated with the aromatic heterocycles of Y1 and Y2, respectively.

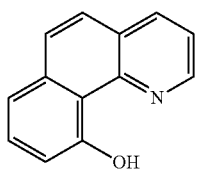 (10)

4-Hydroxy-5-azaphenanthrene forms a complex as follows: the hydrogen atom of its hydroxy group removes and the remaining oxygen atom bonds to a metal atom, and a nitrogen atom in its pyridine skeleton undergoes coordination bonding with the metal atom. Its naphthalene skeleton corresponds to each of A1 and A2, and the pyridine skeleton and the naphthalene skeleton form a fused ring to provide an azaphenanthrene skeleton.

An example of the compound for a ligand in each of the case where X1 represents a structure represented by any one of the formulae (2) to (4) and the case where X2 represents a structure represented by any one of the formulae (6) to (8) is 2-acetylpyrrole represented by the following formula (11).

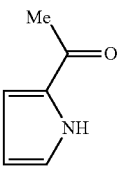 (11)

As shown in Example 3 in Table 10, 2-acetylpyrrole forms a complex as follows: a nitrogen atom in its pyrrole skeleton bonds to a metal atom and the oxygen atom of its acetyl group undergoes coordination bonding with the metal atom. A bond that couples the acetyl group and the pyrrole group to each other corresponds to each of A1 and A2.

TABLE 1

| | Y1 and Y2 | | | | |
|---|---|---|---|---|---|
| X1 and X2 | Hydroxy group / Alkoxy group / Aryloxy group | Carbonyl group | | Alkylthio group / Arylthio group | Thiocarbonyl group |
| *—O—** | 2-methoxyphenol (OMe, OH on benzene) | | | | 2-(methylthio)phenol (SMe, OH on benzene) | |
| *—N—** | N-methyl-2-methoxyethylamine (OMe–CH2CH2–NH–Me) | H–CHO–CH2–NH– (methylaminoacetaldehyde) | Me–CO–CH2–NH– | MeO–CO–CH2–NH– | Me2N–CO–CH2–NH– | N-methyl-2-(methylthio)ethylamine (SMe–CH2CH2–NH–) | CH2=S thioaldehyde–CH2–NH– |
| | 2-(methoxymethyl)pyrrole (OMe–CH2–pyrrole) | pyrrole-2-carbaldehyde (H–CO–pyrrole) | 2-acetylpyrrole (Me–CO–pyrrole) | methyl pyrrole-2-carboxylate (MeO–CO–pyrrole) | N,N-dimethylpyrrole-2-carboxamide (Me2N–CO–pyrrole) | 2-((methylthio)methyl)pyrrole (SMe–CH2–pyrrole) | pyrrole-2-carbothialdehyde (S=CH–pyrrole) |
| *—S—** | 2-methoxyethanethiol (OMe–CH2CH2–SH) | H–CO–CH2–SH | Me–CO–CH2–SH | MeO–CO–CH2–SH | Me2N–CO–CH2–SH | 2-(methylthio)ethanethiol (SMe–CH2CH2–SH) | S=CH–CH2–SH |
| *—CO—O—** | OMe–CH2–CO–OH (methoxyacetic acid) | H–CO–CO–OH | Me–CO–CO–OH (pyruvic acid) | MeO–CO–CO–OH | Me2N–CO–CO–OH | SMe–CH2–CO–OH | S=CH–CO–OH |

TABLE 2
| X1 and X2 | Y1 and Y2 | | |
|---|---|---|---|
| | Amino group | Imino group | Heterocycle |
| *—O—** | 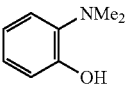 | 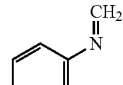 | 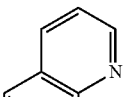 |
| *—N(Me)—** | 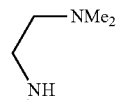 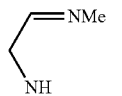 | 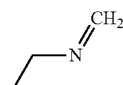 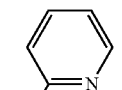 | 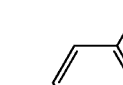 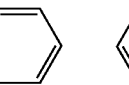 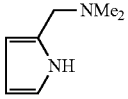 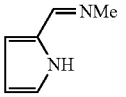 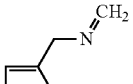 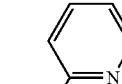 |
| *—S—** | 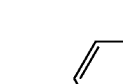 | 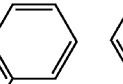 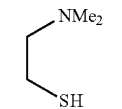 | 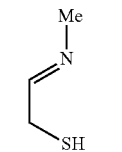 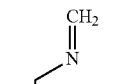 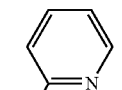 |
| *—CO—O—** | 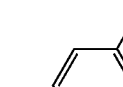 | 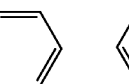 | 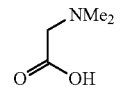 |
| | | | 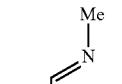 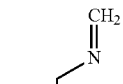 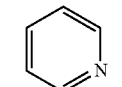   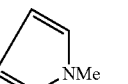 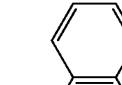 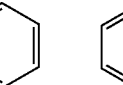 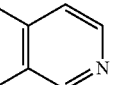 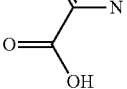  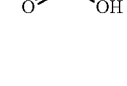 |

TABLE 3
| X1 and X2 | Y1 and Y2 | | | | |
|---|---|---|---|---|---|
| | Hydroxy group Alkoxy group Aryloxy group | Carbonyl group | | | |
| *—O—** | 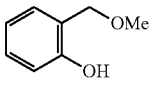 | 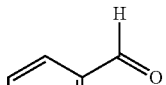 | 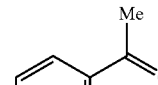 | 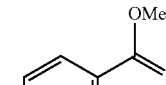 | 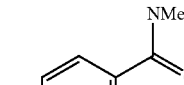 |
| *—N—** | 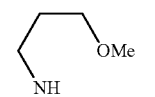 | 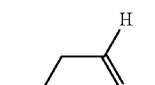 | 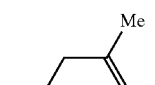 | 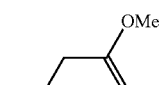 | 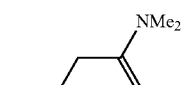 |
| | 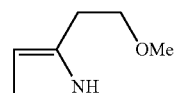 | 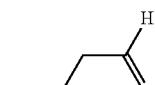 | 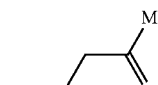 | 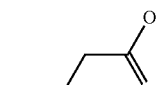 | 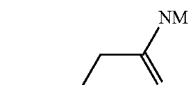 |
| *—S—** | 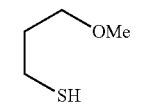 | 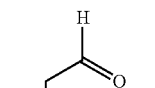 | 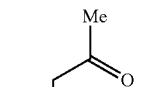 | 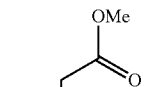 | 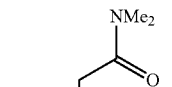 |
| *—CO—O—** | 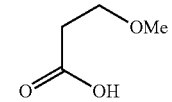 | 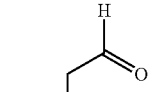 | 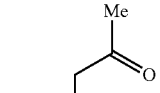 | 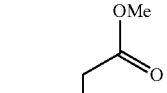 | 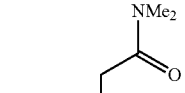 |
| | 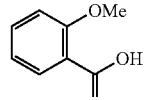 | | | | |
| X1 and X2 | Y1 and Y2 | |
|---|---|---|
| | Alkylthio group Arylthio group | Thiocarbonyl group |
| *—O—** | 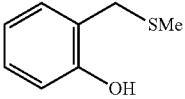 | 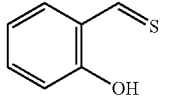 |
| *—N—** | 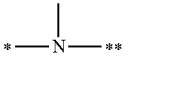 |  |
| | 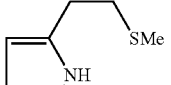 | 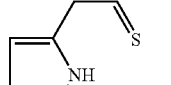 |

TABLE 3-continued
| | | | |
|---|---|---|---|
| | *—S—** | 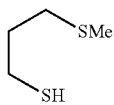 | 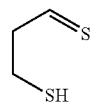 |
| | *—CO—O—** | 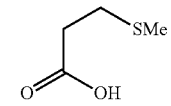 | 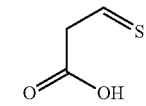 |
| | | 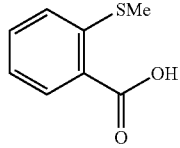 [SMILES: CSc1ccccc1C(=O)O] | |
TABLE 4
| | Y1 and Y2 | | | | |
|---|---|---|---|---|---|
| X1 and X2 | Amino group | Imino group | | Heterocycle | |
| *—O—** | 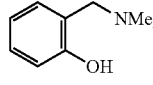 | 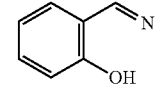 | 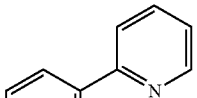 | 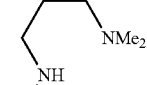 | 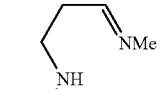 |
| *—N—** | 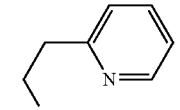 | 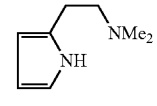 | 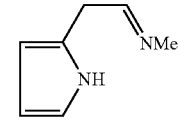 | 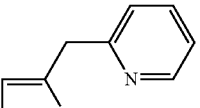 | 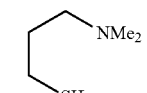 |
| *—S—** | 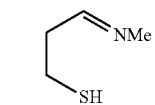 | 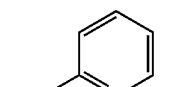 | 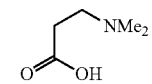 | 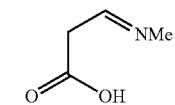 | 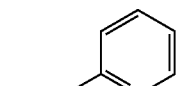 |
| *—CO—O—** | | | | | |

TABLE 4-continued

| | Y1 and Y2 | | |
|---|---|---|---|
| X1 and X2 | Amino group | Imino group | Heterocycle |
| | 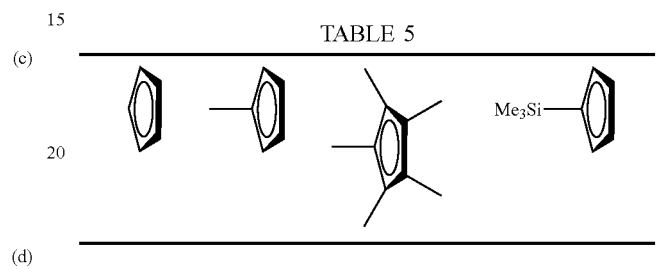 | | |

<Compound represented by formula (c) or (d)>

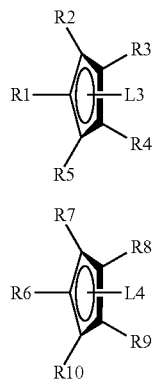

(c)

(d)

In the formula (c), L3 represents a polymetalloxane having a structural unit represented by $M3O_{m/2}$. M3 represents at least one metal atom selected from the group consisting of Ti, Zr, Hf, V, Nb, Ta, W, Al, Ga, In, and Ge, and m represents an integer of 1 or more and q or less when the valence of a metal atom M3 is q. The metal atom M3 in the polymetalloxane may be a plurality of kinds of metal atoms. In addition, the polymetalloxane may have a structural unit represented by $SiO_{s/2}$ (s represents an integer of 1 or more and 4 or less). When the polymetalloxane has the structural unit, the amorphous property of the polymetalloxane improves, and hence the smoothness and strength of a film can be additionally improved.

In the formula (d), L4 represents a metal alkoxide or metal hydroxide having a metal atom M4, and M4 represents at least one metal atom selected from the group consisting of Ti, Zr, Hf, V, Nb, Ta, W, Al, Ga, In, and Ge.

R1 to R5 in the formula (c), and R6 to R10 in the formula (d) each independently represent a hydrogen atom, a linear or branched alkyl group having 1 to 4 carbon atoms, or a trimethylsilyl group. R1 to R5 and R6 to R10 each preferably represent a group showing an electron-donating property in order that the highest occupied molecular orbital (HOMO) of the compound of the present invention may be additionally shallowed. That is, R1 to R5 and R6 to R10 each preferably represent a methyl group, a t-butyl group, or a trimethylsilyl group.

Cyclopentadienyl groups in the formulae (c) and (d) coordinate to the metal atom M3 in L3 and the metal atom M4 in L4, respectively.

With regard to the formulae (c) and (d), specific examples of the compound that coordinates and bonds to a metal atom to form such structure as described above are collectively given in Table 5.

TABLE 5

<Polymetalloxane Having Structure Represented by Formula (e)>

The polymetalloxane according to the formula (e) has a structural unit represented by $M5O_{k/2}$ (M5 represents at least one metal atom selected from the group consisting of Ti, Zr, Hf, V, Nb, Ta, W, Al, Ga, In, and Ge, and k represents an integer of 1 or more and t or less when the valence of a metal atom M1 is t), and the polymetalloxane has a structure represented by the following formula (e).

(e)

$$A5 \underset{X5}{\overset{Y5}{\diamond}} M5$$

In the formula (e), X5 represents any one of the structures represented by the following formulae (12) to (15), and Y5 represents a group having a site that coordinates to M5.

(i) When X5 represents a structure represented by the formula (12), A5 represents an atomic group needed for forming a four- to eight-membered ring together with M5, X5, and Y5, the atomic group containing an aromatic ring, and one constituent carbon atom of the aromatic ring is bonded to the oxygen atom of X5, and (ii) when X5 represents a structure represented by any one of the formulae (13) to (15), A5 represents a bond or atomic group needed for forming a four- to eight-membered ring together with M5, X5, and Y5.

 (12)

 (13)

 (14)

 (15)

(In the formulae (12) to (15), * represents a bonding site with A5 and ** represents a bonding site with M5.)

It should be noted that A5, X5, and Y5 are identical in meaning to A1, X1, and Y1 in the formula (a), respectively. In addition, a preferred combination of A5, X5, and Y5 in the formula (e) is the same as that obtained by replacing A1 with A5, X1 with X5, and Y1 with Y5, respectively in the preferred combination of A1, X1, and Y1.

Further, the ring formed by A5, M5, X5, and Y5 is preferably a five- or six-membered ring from the viewpoint of the ease with which a complex is formed.

In addition, examples of the compound that coordinates and bonds to the metal atom M5 to form a structure represented by the formula (e) (compound for a ligand) include the compounds shown in Tables 1 to 4.

In addition, the polymetalloxane according to the formula (e) may have a structural unit represented by $SiO_{i/2}$ (i represents an integer of 1 or more and 4 or less). When the polymetalloxane has the structural unit, the amorphous property of the polymetalloxane improves, and hence the smoothness and strength of a film can be additionally improved.

<Polymetalloxane Having Structure Represented by Formula (f)>

The polymetalloxane according to the formula (f) has a structural unit represented by $M6O_{u/2}$ (M6 represents at least one metal atom selected from the group consisting of Ti, Zr, Hf, V, Nb, Ta, W, Al, Ga, In, and Ge, and 1 represents an integer of 1 or more and u or less when the valence of a metal atom M6 is u), and the polymetalloxane has a structure represented by the following formula (f).

(f)

In the formula (f), R61 to R65 each independently represent a hydrogen atom, an alkyl group having 1 to 4 carbon atoms, or a trimethylsilyl group, and a cyclopentadienyl group coordinates to M6.

R61 to R63 each preferably represent a group showing an electron-donating property in order that the highest occupied molecular orbital (HOMO) of the polymetalloxane having a structure represented by the formula (f) may be additionally shallowed. That is, R61 to R63 each preferably represent a methyl group, a t-butyl group, or a trimethylsilyl group.

In addition, examples of the compound that coordinates to the metal atom M6 to form a structure represented by the formula (f) (compound for a ligand) include the compounds shown in Table 5.

In addition, the polymetalloxane having a structure represented by the formula (f) may have a structural unit represented by $SiO_{j/2}$ (j represents an integer of 1 or more and 4 or less). When the polymetalloxane has the structural unit, the amorphous property of the polymetalloxane improves, and hence the smoothness and strength of a film can be additionally improved.

With regard to the formulae (a) to (f), the number of compounds that coordinate to one metal atom is not limited to one. In addition, the number of kinds of compounds that coordinate to the metal atom is not limited to one and a plurality of kinds of compounds may coordinate to the metal atom.

[Support]

The support needs to have rigidity sufficient for contact with a photosensitive member and a metal material is preferably used therefor. Specific examples of the metal material include iron, copper, stainless steel, aluminum, an aluminum alloy, and nickel. In addition, a support made of a resin reinforced with a filler can be used.

[Elastic Layer]

One or two or more kinds of elastic bodies such as a rubber and thermoplastic elastomer that have heretofore been used in the elastic layers of charging members can each be used as a material for forming the elastic layer.

Specific examples of the rubber include a urethane rubber, a silicone rubber, a butadiene rubber, an isoprene rubber, a chloroprene rubber, a styrene-butadiene rubber, an ethylene-propylene rubber, a polynorbornene rubber, an acrylonitrile rubber, an epichlorohydrin rubber, and an alkyl ether rubber. Examples of the thermoplastic elastomer include a styrene-based elastomer and an olefin-based elastomer.

The elastic layer is preferably formed so as to have predetermined conductivity by containing a conductive agent. A suitable range of the electrical resistance value of the elastic layer is $10^2 \Omega$ or more and $10^8 \Omega$ or less.

As the conductive agent to be used for the conductive elastic layer, there can be used a carbon-based material, a metal oxide, a metal, a cationic surfactant, an anionic surfactant, a zwitterionic surfactant, an antistatic agent, an electrolyte, or the like.

Specific examples of the carbon-based material include conductive carbon black and graphite. Specific examples of the metal oxide include tin oxide, titanium oxide, and zinc oxide. Specific examples of the metal include nickel, copper, silver, and germanium.

Specific examples of the cationic surfactant include quaternary ammonium salts (such as lauryltrimethylammonium, stearyltrimethylammonium, octadecyltrimethylammonium, dodecyltrimethylammonium, hexadecyltrimethylammonium, and a modified fatty acid-dimethylethylammonium), perchloric acid salts, chloric acid salts, fluoroboric acid salts, ethosulfate salts, and benzyl halide salts (such as benzyl bromide salt and benzyl chloride salt).

Specific examples of the anionic surfactant include an aliphatic sulfonic acid salt, a higher alcohol sulfuric acid ester salt, a higher alcohol ethylene oxide adduct sulfuric acid ester salt, a higher alcohol phosphoric acid ester salt, and a higher alcohol ethylene oxide adduct phosphoric acid ester salt.

Examples of the antistatic agent include non-ionic antistatic agents such as a higher alcohol ethylene oxide, a polyethylene glycol fatty acid ester, and a polyhydric alcohol fatty acid ester.

Examples of the electrolyte include salts (e.g., quaternary ammonium salts) of metals of the first group of the periodic table (such as Li, Na, and K). Specific examples of the salts of metals of the first group of the periodic table include $LiCF_3SO_3$, $NaClO_4$, $LiAsF_6$, $LiBF_4$, NaSCN, KSCN, and NaCl.

Further examples of the conductive agent to be used for the conductive elastic layer include salts of metals of the second group of the periodic table (such as Ca and Ba) (e.g., $Ca(ClO_4)_2$) and antistatic agents derived therefrom. Alternatively, there can be used ion-conductive conductive agents such as complexes of those conductive agents with polyhydric alcohols (such as 1,4-butanediol, ethylene glycol, polyethylene glycol, propylene glycol, and polypropylene glycol) or derivatives thereof and complexes of those conductive agents with monools (such as ethylene glycol monomethyl ether and ethylene glycol monoethyl ether).

The hardness of the elastic layer is preferably 60° or more and 85° or less in terms of MD-1 hardness from the viewpoint of suppressing the deformation of the charging member when the charging member and a photosensitive member as a body to be charged are brought into contact with each other. In addition, the elastic layer is preferably of the so-called crown shape in which the thickness of a central portion is larger than the thickness of an end portion in order that the charging member may be uniformly brought into contact with the photosensitive member in its width direction.

[Formation of Surface Layer]

The surface layer according to the present invention is formed by drying a coating film of a coating liquid on the support or on the elastic layer.

The coating liquid can be obtained by mixing a metal alkoxide and the compound for a ligand described in the foregoing in an organic solvent. If available, a metal alkoxide to which a compound coordinates can be obtained and used as it is.

As the metal alkoxide, there can be used alkoxides of titanium, zirconium, hafnium, vanadium, niobium, tantalum, tungsten, aluminum, gallium, indium, and germanium. Examples of the alkoxide include methoxide, ethoxide, n-propoxide, iso-propoxide, n-butoxide, 2-butoxide, and t-butoxide.

The compound for a ligand is added in an amount of preferably 0.5 mol or more, more preferably 1 mol or more with respect to 1 mol of the metal alkoxide. In addition, a plurality of compounds or metal alkoxides may be used in combination.

In the compound according to the present invention, the fact that the metal atom and the compound for a ligand are bonded to each other can be confirmed by performing $^1$H-NMR analysis.

Water, an acid, or a base can be added as a catalyst as required in order that the metal alkoxide may be condensed to provide a polymetalloxane. In addition, the condensation may be accelerated by heating the coating liquid. In the coating liquid obtained by mixing the compound and the metal alkoxide, the condensation of the metal alkoxide does not progress to a very large extent, and it is assumed that the metal alkoxide may be condensed in the step of applying the coating liquid onto the elastic layer, followed by the drying of the liquid (described later). When the metal alkoxide and the compound for a ligand are mixed, and the condensation of the metal alkoxide is accelerated through the addition of the catalyst to the coating liquid or the heating of the liquid, the energy level of the highest occupied molecular orbital (HOMO) of the compound according to the present invention is additionally shallowed, and hence an electron is easily discharged. Accordingly, a discharge start voltage reduces, and hence local and strong discharge (abnormal discharge) can be suppressed. When water is added, the addition amount of water is preferably from 0.01 mol to 5 mol, more preferably from 0.1 mol to 3 mol with respect to 1 mol of the metal alkoxide.

In order to improve film properties of the surface layer of the present invention (smoothness and strength of the film), an alkoxysilane can be added to the coating liquid. A tetraalkoxysilane, a trialkoxysilane, or a dialkoxysilane is used as the alkoxysilane.

Specific examples of the tetraalkoxysilane include tetramethoxysilane, tetraethoxysilane, tetra(n-propoxy)silane, tetra(iso-propoxy)silane, tetra(n-butoxy)silane, tetra(2-butoxy)silane, and tetra(t-butoxy) silane.

Examples of the trialkoxysilane include: trimethoxysilanes such as trimethoxyhydrosilane, trimethoxymethylsilane, trimethoxyethylsilane, trimethoxy(n-propyl)silane, trimethoxy(iso-propoxy)silane, trimethoxy(n-butoxy)silane, trimethoxy(2-butoxy)silane, trimethoxy(t-butoxy)silane, trimethoxy(n-hexyl)silane, trimethoxy(n-octyl)silane, trimethoxy(n-decyl)silane, trimethoxy(n-dodeca)silane, trimethoxy(n-tetradeca)silane, trimethoxy(n-pentadeca)silane, trimethoxy(n-hexadeca)silane, trimethoxy(n-octade)silane, trimethoxycyclohexylsilane, trimethoxyphenylsilane, and trimethoxy(3-glycidylpropyl)silane; and triethoxysilanes such as triethoxyhydrosilane, triethoxymethylsilane, triethoxyethylsilane, triethoxy(n-propyl)silane, triethoxy(iso-propoxy)silane, triethoxy(n-butoxy)silane, triethoxy(2-butoxy)silane, triethoxy(t-butoxy)silane, triethoxy(n-hexyl)silane, triethoxy(n-octyl)silane, triethoxy(n-decyl)silane, triethoxy(n-dodeca)silane, triethoxy(n-tetradeca)silane, triethoxy(n-pentadeca)silane, triethoxy(n-hexadeca)silane, triethoxy(n-octade)silane, triethoxycyclohexylsilane, triethoxyphenylsilane, and triethoxy(3-glycidylpropyl)silane.

Specific examples of the dialkoxysilane include: dimethoxysilanes such as dimethoxydimethylsilane, dimethoxydiethylsilane, dimethoxymethylphenylsilane, dimethoxydiphenylsilane, and dimethoxy(bis-3-glycidylpropyl)silane; and diethoxysilanes such as diethoxydimethylsilane, diethoxydiethylsilane, diethoxymethylphenylsilane, diethoxydiphenylsilane, and diethoxy(bis-3-glycidylpropyl) silane.

The organic solvent to be used is not particularly limited as long as the organic solvent can dissolve the metal alkoxide and the above-mentioned compound. There can be used an alcohol-based solvent, an ether-based solvent, a cellosolve-based solvent, a ketone-based solvent, an ester-based solvent, or the like. Specific examples of the alcohol-based solvent include methanol, ethanol, n-propanol, iso-propanol, 1-butanol, 2-butanol, t-butanol, 1-pentanol, and cyclohexanol. A specific example of the ether-based solvent is dimethoxyethane. Specific examples of the cellosolve-based solvent include methyl cellosolve and ethyl cellosolve. Specific examples of the ketone-based solvent include acetone, methyl ethyl ketone, and methyl iso-butyl ketone. Specific examples of the ester-based solvent include methyl acetate and ethyl acetate. One kind of the organic solvents may be used alone, or a mixture of two or more kinds thereof may be used.

A method of forming the surface layer is not particularly limited and a method to be generally employed can be selected. Specific examples thereof include application with a roll coater, immersion application, and ring application.

After the formation of the surface layer, the layer can be subjected to a heat treatment in order that the solvent may be dried.

In addition, subjecting the surface layer to a surface treatment can adjust surface physical properties such as dynamic friction and surface free energy. Specifically, a method involving irradiating the layer with an active energy ray is available, and examples of the active energy ray include UV light, an infrared ray, and an electron beam.

The thickness of the surface layer is preferably from 0.005 µm to 30 µm, more preferably from 0.005 µm to 5 µm from the viewpoint of additionally suppressing the occurrence of the abnormal discharge.

<Electrophotographic Apparatus and Process Cartridge>

Figure 2:
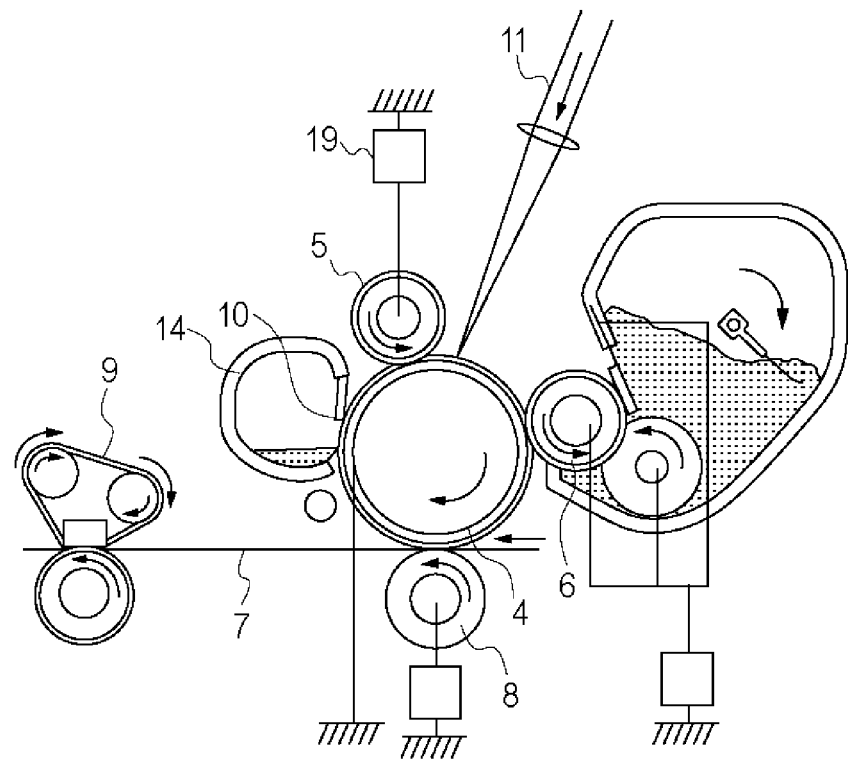
FIG. 2 is a sectional view of an example of an electrophotographic apparatus of the present invention.
Figure 3:
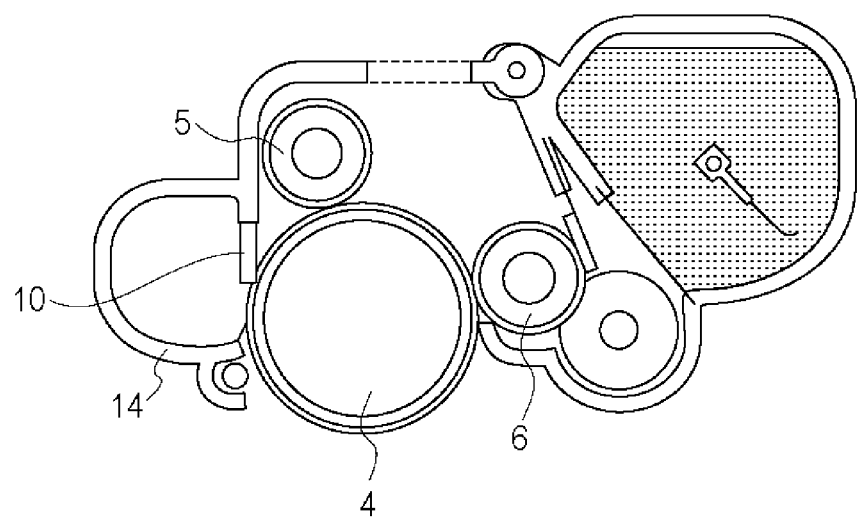
FIG. 3 is a sectional view of an example of a process cartridge of the present invention.

FIG. 2 illustrates an example of an electrophotographic apparatus including the charging member of the present invention, and FIG. 3 illustrates an example of a process cartridge including the charging member of the present invention.

A photosensitive member 4 is an image-bearing member of a rotating drum type. The photosensitive member is rotationally driven in a clockwise direction indicated by an arrow in the figure at a predetermined peripheral speed.

A charging roller 5 is a charging member. Charging means is constituted of a charging bias-applying power source 19 that applies a charging bias to the charging roller 5. The charging roller 5 is brought into contact with the surface of the photosensitive member 4 with a predetermined pressing force, and is rotationally driven in a forward direction with respect to the rotation of the photosensitive member 4. When a predetermined DC voltage (set to −1,050 V in Examples to be described later) is applied from the charging bias-applying power source 19 to the charging roller 5 (DC charging system), the surface of the photosensitive member 4 is uniformly subjected to a charging treatment to a predetermined polar potential (set to a dark portion potential of −500 V in Examples to be described later).

Image exposure corresponding to target image information is formed on the surface of the photosensitive member 4 subjected to the charging treatment by exposing means 11. The potential of the exposure light portion of the charged surface of the photosensitive member (set to a light portion potential of −150 V in Examples to be described later) selectively reduces (attenuates), and hence an electrostatic latent image is formed on the photosensitive member 4. Known means can be utilized as the exposing means 11 and a laser beam scanner can be given as a suitable example thereof.

A development roller 6 causes a toner (negative toner) charged to the same polarity as the charged polarity of the photosensitive member 4 to selectively adhere to the exposure light portion of the electrostatic latent image on the surface of the photosensitive member 4 to visualize the electrostatic latent image as a toner image. In Examples to be described later, its developing bias was set to −400 V. A development system is not particularly limited, and for example, a jumping development system, a contact development system, and a magnetic brush system are available. Of those, a contact development system can be said to be preferred particularly for an electrophotographic apparatus that outputs a color image for the purpose of, for example, alleviating the scattering property of the toner.

A transfer roller 8 is brought into contact with the photosensitive member 4 with a predetermined pressing force, and rotates in the forward direction with respect to the rotation of the photosensitive member 4 at substantially the same peripheral speed as the rotational peripheral speed of the photosensitive member 4. In addition, a transfer voltage having polarity opposite to the charged characteristic of the toner is applied from a transfer bias-applying power source. A transfer material 7 is fed from a sheet-feeding mechanism (not shown) to a contact portion between the photosensitive member 4 and the transfer roller 8 at a predetermined timing, and the back surface of the transfer material 7 is charged to the polarity opposite to the charged polarity of the toner by the transfer roller 8 to which the transfer voltage has been applied. Thus, in the contact portion between the photosensitive member 4 and the transfer roller 8, a toner image on a photosensitive member surface side is electrostatically transferred onto the surface side of the transfer material 7. Known means can be utilized as the transfer roller 8. A transfer roller obtained by covering the top of a conductive support such as a metal with an elastic layer whose resistance has been adjusted to a middle value can be given as an example thereof.

The transfer material 7 onto which the toner image has been transferred is separated from the photosensitive member surface and introduced into a fixing apparatus 9. The toner image is fixed in the apparatus and the resultant is output as an image-formed product. In the case of a two-sided image formation mode or a multiple image formation mode, the image-formed product is introduced into a recirculation conveying mechanism (not shown) and reintroduced into a transfer portion. A residue on the photosensitive member 4 such as transfer residual toner is recovered from the photosensitive member 4 by a cleaning apparatus 14 having a cleaning blade 10.

In addition, when residual charge remains on the photosensitive member 4, it is recommended that the residual charge on the photosensitive member 4 be removed by a pre-exposure apparatus (not shown) after the transfer before primary charging by the charging roller 5 is performed. In image formation in Examples to be described later, there was used an electrophotographic apparatus that did not use any pre-exposure apparatus.

The process cartridge according to the present invention integrally supports at least the charging member and a photosensitive member, and is removably mounted onto the main body of an electrophotographic apparatus. In Examples to be described later, there was used a process cartridge integrally supporting the charging roller 5, the photosensitive member 4, the development roller 6, and the cleaning apparatus 14.

EXAMPLES

Hereinafter, the present invention is described in more detail by way of specific Examples. With regard to compounds in Examples, the term "part(s)" refers to "part(s) by mass" unless otherwise specified.

Table 9 shows the list of reagents used below. In addition, Table 10 shows the coordination structures of compounds used in Examples with respect to metal atoms.

Example 1

[Production of Conductive Elastic Roller A]

Materials shown in Table 6 were mixed with a 6-L pressure kneader (trade name: TD6-15MDX, manufactured by Toshin Co., Ltd.) at a filling ratio of 70 vol % and a blade revolution number of 30 rpm for 24 minutes to provide an unvulcanized rubber composition. 4.5 Parts of tetrabenzylthiuram disulfide [trade name: SANCELER TBzTD, manufactured by SANSHIN CHEMICAL INDUSTRY CO., LTD.] as a vulcanization accelerator and 1.2 parts of sulfur as a vulcanizing agent were added to 174 parts by mass of the unvulcanized rubber composition. Then, the mixture was subjected to transverse crosscutting with open rolls each having a roll diameter of 12 inches at a front roll revolution number of 8 rpm, a rear roll revolution number of 10 rpm, and a roll interval of 2 mm a total of 20 times. After that, the roll interval was set to 0.5 mm and the resultant was subjected to tight milling 10 times to provide a "kneaded product A" for a conductive elastic layer.

TABLE 6

| Raw material | Usage |
| --- | --- |
| Medium high nitrile NBR (trade name: Nipol DN219, manufactured by Zeon Corporation) | 100 parts |
| Carbon black for colors (trade name: #7360, manufactured by TOKAI CARBON CO., LTD.) | 48 parts |
| Calcium carbonate (trade name: NANOX #30, manufactured by MARUO CALCIUM CO., LTD.) | 20 parts |
| Zinc oxide | 5 parts |
| Stearic acid | 1 part |

Next, a columnar support made of steel having a diameter of 6 mm and a length of 252 mm (its surface had been subjected to nickel plating processing and the support is hereinafter referred to as "mandrel") was prepared. Then, a thermosetting adhesive containing a metal and a rubber (trade name: METALOC U-20, manufactured by TOYOKAGAKU KENKYUSHO CO., LTD.) was applied to a region extending toward both sides with respect to a center in an axial direction on the mandrel by 115.5 mm each (region having a axial direction width of 231 mm in total). The adhesive was dried at a temperature of 80° C. for 30 minutes and was then further dried at 120° C. for 1 hour.

The kneaded product A was simultaneously extruded into a cylindrical shape having an outer diameter of from 8.75 to 8.90 mm by extrusion molding with a crosshead in a concentric manner about the mandrel with the adhesive layer, followed by the cutting of its end portions. Thus, an unvulcanized conductive elastic layer was laminated on the outer periphery of the mandrel. An extruder having a cylinder diameter of 70 mm and a ratio L/D of 20 was used as an extruder, and the temperatures of a head, a cylinder, and a screw at the time of the extrusion were controlled to 90° C.

Next, the resultant roller was vulcanized with a continuous heating furnace having 2 zones set to different temperatures. The temperature of a first zone was set to 80° C. and the roller was passed therethrough for 30 minutes. The temperature of a second zone was set to 160° C. and the roller was similarly passed therethrough for minutes. Thus, a conductive elastic roller 1 was obtained.

Next, both ends of the conductive elastic layer portion (rubber portion) of the conductive elastic roller 1 were cut so that the axial direction width of the conductive elastic layer portion became 232 mm. After that, the surface of the conductive elastic layer portion was polished with a rotary grindstone (work revolution number: 333 rpm, grindstone revolution number: 2,080 rpm, polishing time: 12 sec). Thus, the conductive elastic roller 1 of a crown shape having an end portion diameter of 8.26 mm and a central portion diameter of 8.50 mm whose surface had a ten-point average roughness Rz of 5.5 μm, a run-out of 18 μm, and a hardness of 73° (Asker C) was obtained.

The ten-point average roughness Rz was measured in conformity with JIS B6101. The run-out was measured with a high-accuracy laser measuring machine LSM430v manufactured by Mitutoyo Corporation. Specifically, outer diameters were measured with the measuring machine, and a difference between the maximum outer diameter value and the minimum outer diameter value was defined as an outer diameter difference run-out. The measurement was performed at 5 points and the average of the 5 outer diameter difference run-outs was defined as the run-out of the measured object. The Asker C hardness was measured in a measurement environment having a temperature of 25° C. and a humidity of 55% RH by bringing the press needle of an Asker C-type hardness meter (manufactured by KOBUNSHI KEIKI CO., LTD.) into contact with the surface of the measuring object under a condition of a load of 1,000 g.

[Preparation of Coating Liquid E1]

15.1 Grams of 2-butanol and 0.74 g of titanium isopropoxide were weighed in a 100-mL container made of glass, and were stirred and dissolved to prepare a titanium isopropoxide/2-butanol solution. 0.32 Gram of guaiacol and 34.0 g of ethanol were weighed in another container, and were stirred and dissolved to prepare a guaiacol/ethanol solution. The guaiacol/ethanol solution was added to the titanium isopropoxide/2-butanol solution prepared in advance, and the mixture was stirred well to prepare a coating liquid E1.

[Structural Analysis]

The structure of a compound in the coating liquid E1 was estimated as described below.

Figure 4:
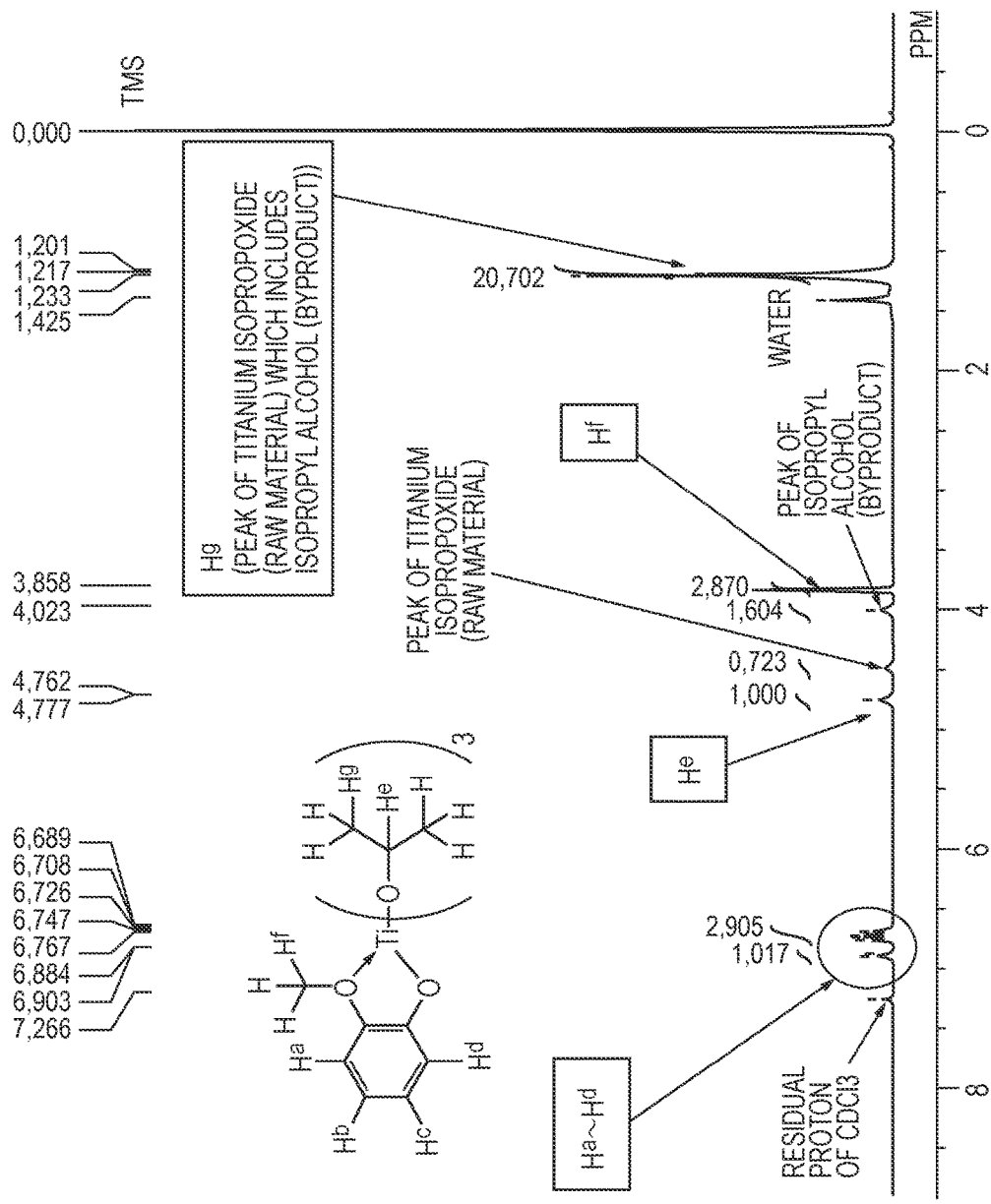
FIG. 4 shows the results of the $^1$H-NMR spectral analysis of an example of a compound contained in a surface layer of the present invention.

In deuterated chloroform, titanium isopropoxide and guaiacol were stirred at room temperature to be caused to react with each other. The structure of the resultant compound was identified by employing $^1$H-NMR. As a result, as shown in FIG. 4, a structure in which guaiacol coordinated to titanium was suggested.

[Formation of Surface Layer]

The coating liquid E1 was applied onto the conductive elastic layer roller A by ring application at an ejection amount of 0.120 ml/s (speed of a ring portion: 85 mm/s, total ejection amount: 0.130 ml). The liquid was left to stand at normal temperature and normal pressure to be dried, and then the roller was irradiated with UV light having a wavelength of 254 nm so that an integrated light quantity became 9,000 mJ/cM2. Thus, a surface layer was formed. A low-pressure mercury lamp [manufactured by HARISON TOSHIBA LIGHTING CORPORATION] was used in the UV light irradiation. Thus, a charging member E1 was produced.

[Evaluation]

A charging roller mounted on a cyan cartridge for a laser printer (trade name: HP Color Laser Jet CP4525, manufactured by Hewlett-Packard Company) was replaced with the charging member E1 produced in advance. The cartridge was set in the laser printer (trade name: HP Color Laser Jet CP4525, manufactured by Hewlett-Packard Company), and a halftone image was formed on A4 size paper. It should be noted that at the time of the formation of the electrophotographic image, no pre-exposure was performed, and a charging voltage was set to −1,141 V and a transfer voltage was set to 1,856 V. The setting is intended for the establishment of an environment where abnormal discharge is additionally liable to occur. In addition, the electrophotographic image was output under a low-temperature and low-humidity environment (having a temperature of 15° C. and a humidity of 10%).

Then, the resultant halftone image was evaluated for whether abnormal discharge occurred by visually observing the presence or absence of an uneven image resulting from the abnormal discharge.

A: Abnormal discharge is absent.
B: Abnormal discharge is present.
As a result, no abnormal discharge was observed in the charging member E1.

Comparative Example 1

15.0 Grams of 2-butanol, 1.78 g of titanium isopropoxide, and 33.2 g of ethanol were weighed in a 100-mL container made of glass, and were stirred and dissolved to prepare a coating liquid C1. A charging member C1 was produced and subjected to the evaluation in the same manner as in Example 1 except that the coating liquid C1 was used.

Abnormal discharge was observed in the charging member C1.

Examples 2 to 9

A coating liquid E2 was prepared in the same manner as in Example 1 except that weights were changed.

In addition, a coating liquid E3, a coating liquid E4, a coating liquid E5, a coating liquid E6, a coating liquid E7, and a coating liquid E9 were prepared by the same method as that of Example 1 except that 2-acetylpyrrole, 2-(methylthio)phenol, methyl 3-hydroxy-2-naphthoate, quinaldic acid, N,N-dimethylglycine, and 2-amino-p-cresol were used instead of guaiacol, respectively. Table 7-1 collectively shows the weights of the respective compounds.

A coating liquid E8 was prepared by the same method as that of Example 1 except that: pentamethylcyclopentadienyl titanium trimethoxide was used instead of titanium isopropoxide; and guaiacol was not added. Table 7-1 collectively shows the weights.

Charging members E2 to E9 were produced and subjected to the evaluation in the same manner as in Example 1 except that the coating liquids E2 to E9 were used, respectively. Table 8-1 collectively shows the results of the evaluation.

TABLE 7-1

| | Coating liquid | Metal alkoxide | | Compound for ligand | | 2-Butanol | Ethanol | Ion-exchanged water | Solid matter | |
|---|---|---|---|---|---|---|---|---|---|---|
| Example 1 | E1 | Titanium isopropoxide | 0.74 g | Guaiacol | 0.32 g | 15.1 g | 34.0 g | — | 0.53 g | 1.0% |
| Example 2 | E2 | Titanium isopropoxide | 0.46 g | Guaiacol | 0.40 g | 15.1 g | 34.3 g | — | 0.53 g | 1.0% |
| Example 3 | E3 | Titanium isopropoxide | 0.79 g | 2-Acetylpyrrole | 0.30 g | 15.1 g | 34.0 g | — | 0.52 g | 1.0% |
| Example 4 | E4 | Titanium isopropoxide | 0.68 g | 2-(Methylthio)phenol | 0.34 g | 15.0 g | 34.0 g | — | 0.53 g | 1.1% |
| Example 5 | E5 | Titanium isopropoxide | 0.54 g | Methyl 3-hydroxy-2-naphthoate | 0.37 g | 15.0 g | 34.2 g | — | 0.52 g | 1.0% |
| Example 6 | E6 | Titanium isopropoxide | 0.58 g | Quinaldic acid | 0.35 g | 15.1 g | 34.4 g | — | 0.51 g | 1.0% |
| Example 7 | E7 | Titanium isopropoxide | 0.81 g | N,N-Dimethylglycine | 0.30 g | 15.0 g | 33.9 g | — | 0.52 g | 1.0% |
| Example 8 | E8 | Pentamethylcyclopentadienyl titanium trimethoxide | 0.67 g | — | — | 15.1 g | 34.3 g | — | 0.50 g | 1.0% |
| Example 9 | E9 | Titanium isopropoxide | 0.73 g | 2-Amino-p-cresol | 0.33 g | 15.0 g | 34.2 g | — | 0.53 g | 1.1% |
| Comparative Example 1 | C1 | Titanium isopropoxide | 1.78 g | — | — | 15.0 g | 33.2 g | — | 0.50 g | 1.0% |

Examples 10 to 14

A coating liquid E10, a coating liquid E11, and coating liquids E12 to E14 were prepared by the same method as that of Example 1 except that aluminum sec-butoxide, zirconium(IV) propoxide, and tungsten(V) ethoxide were used instead of titanium isopropoxide, respectively. Table 7-2 collectively shows the weights.

Charging members E10 to E14 were produced and subjected to the evaluation in the same manner as in Example 1 except that the coating liquids E10 to E14 were used, respectively. Table 8-2 collectively shows the results of the evaluation.

Comparative Examples 2 to 4

A coating liquid C2, a coating liquid C3, and a coating liquid C4 were prepared by the same method as that of Comparative Example 1 except that aluminum sec-butoxide, a 70 mass % solution of zirconium(IV) propoxide in 1-propanol, and tungsten(V) ethoxide were used instead of titanium isopropoxide, respectively. Table 7-2 collectively shows the weights.

Charging members C2 to C4 were produced and subjected to the evaluation in the same manner as in Example 1 except that the coating liquids C2 to C4 were used, respectively. Table 8-2 collectively shows the results of the evaluation.

TABLE 7-2

| | Coating liquid | Metal alkoxide | | Compound for ligand | | 2-Butanol | Ethanol | Solid matter | |
|---|---|---|---|---|---|---|---|---|---|
| Example 10 | E10 | Aluminum sec-butoxide | 0.73 g | Guaiacol | 0.38 g | 15.0 g | 34.0 g | 0.53 g | 1.1% |
| Comparative Example 2 | C2 | Aluminum sec-butoxide | 2.41 g | — | — | 15.0 g | 32.5 g | 0.50 g | 1.0% |

TABLE 7-2-continued

| | Coating liquid | Metal alkoxide | | Compound for ligand | | 2-Butanol | Ethanol | Solid matter | |
|---|---|---|---|---|---|---|---|---|---|
| Example 11 | E11 | Zirconium(IV) propoxide | 0.71 g | Guaiacol | 0.20 g | 15.1 g | 34.2 g | 0.47 g | 0.9% |
| Comparative Example 3 | C3 | Zirconium(IV) propoxide | 2.23 g | — | — | 15.0 g | 32.6 g | 0.59 g | 1.2% |
| Example 12 | E12 | Tungsten(V) ethoxide | 0.37 g | Guaiacol | 0.34 g | 15.1 g | 34.3 g | 0.54 g | 1.1% |
| Example 13 | E13 | Tungsten(V) ethoxide | 0.46 g | Guaiacol | 0.28 g | 15.1 g | 34.3 g | 0.53 g | 1.1% |
| Example 14 | E14 | Tungsten(V) ethoxide | 0.61 g | Guaiacol | 0.20 g | 15.0 g | 34.3 g | 0.53 g | 1.1% |
| Comparative Example 4 | C4 | Tungsten(V) ethoxide | 0.85 g | — | — | 15.1 g | 34.2 g | 0.46 g | 0.9% |

Example 15

15.0 Grams of 2-butanol and 0.58 g of titanium isopropoxide were weighed in a 100-mL container made of glass, and were stirred and dissolved to prepare titanium isopropoxide/2-butanol. 0.35 Gram of quinaldic acid and 20.0 g of ethanol were weighed in another container, and were stirred and dissolved to prepare a quinaldic acid/ethanol solution. The quinaldic acid/ethanol solution was added to the titanium isopropoxide/2-butanol solution prepared in advance, and the contents were stirred and dissolved to prepare a titanium isopropoxide-quinaldic acid/2-butanol-ethanol solution. 0.12 Gram of ion-exchanged water and 13.9 g of ethanol were weighed in still another container, and were stirred and dissolved to prepare an ion-exchanged water/ethanol solution. The ion-exchanged water/ethanol solution was added to the titanium isopropoxide-quinaldic acid/2-butanol-ethanol solution prepared in advance, and the contents were stirred and dissolved to prepare a coating liquid E15.

A charging member E15 was produced and subjected to the evaluation in the same manner as in Example 1 except that the coating liquid E15 was used. Table 8-3 shows the result of the evaluation.

In addition, the structure of a compound in the coating liquid E15 was estimated as described below.

In deuterated chloroform, titanium isopropoxide and guaiacol were stirred at room temperature. After that, a liquid prepared by dissolving a small amount of water in deuterated methanol was added to the mixture, and the whole was subjected to a reaction. The structure of the resultant compound was identified by employing $^1$H-NMR. As a result, as shown in FIG. 5, a peak on a benzene ring on guaiacol that had coordinated to titanium is broadened, which suggested an increase in molecular weight. That is, a titanium atom to which guaiacol has coordinated can be interpreted as bonding to another titanium atom through an oxygen atom.

Example 16

15.1 Grams of 2-butanol, 0.42 g of titanium isopropoxide, and 0.24 g of trimethoxy(n-propyl)silane were weighed in a 100-mL container made of glass, and were stirred and dissolved to prepare a titanium isopropoxide-trimethoxy(n-propyl)silane/2-butanol solution. 0.26 Gram of quinaldic acid and 20.0 g of ethanol were weighed in another container, and were stirred and dissolved to prepare a quinaldic acid/ethanol solution. The quinaldic acid/ethanol solution was added to the titanium isopropoxide-trimethoxy(n-propyl)silane/2-butanol solution prepared in advance to prepare a titanium isopropoxide-trimethoxy(n-propyl) silane-quinaldic acid/2-butanol-ethanol solution. 0.16 Gram of ion-exchanged water and 14.1 g of ethanol were weighed in still another container, and were stirred and dissolved to prepare an ion-exchanged water/ethanol solution. The ion-exchanged water/ethanol solution was added to the titanium isopropoxide-trimethoxy(n-propyl) silane-quinaldic acid/2-butanol-ethanol solution prepared in advance, and the contents were stirred well and dissolved to prepare a coating liquid E16. Table 7-3 similarly shows the weights.

A charging member E16 was produced and subjected to the evaluation in the same manner as in Example 1 except that the coating liquid E16 was used. Table 8-3 shows the result of the evaluation.

Comparative Example 5

15.0 Grams of 2-butanol, 0.82 g of titanium isopropoxide, and 0.46 g of trimethoxy(n-propyl)silane were weighed in a 100-mL container made of glass, and were stirred and dissolved to prepare a titanium isopropoxide-n-propyltrimethoxysilane/2-butanol solution. 0.37 Gram of ion-exchanged water and 33.5 g of ethanol were weighed in another container, and were stirred to prepare an ion-exchanged water/ethanol solution. The ion-exchanged water/ethanol solution was added to the titanium isopropoxide-trimethoxy(n-propyl)silane/2-butanol solution prepared in advance, and the contents were stirred well and dissolved to prepare a coating liquid C5. Table 7-3 similarly shows the weights.

A charging member C5 was produced and subjected to the evaluation in the same manner as in Example 1 except that the coating liquid C5 was used. Table 8-3 shows the result of the evaluation.

TABLE 7-3

| | Coating liquid | Metal alkoxide | | Compound for ligand | | Alkoxysilane | | 2-Butanol |
|---|---|---|---|---|---|---|---|---|
| Example 15 | E15 | Titanium isopropoxide | 0.58 g | Quinaldic acid | 0.35 g | — | — | 15.1 g |

TABLE 7-3-continued

|  | Coating liquid | Metal alkoxide | | Compound for ligand | | Alkoxysilane | | 2-Butanol |
|---|---|---|---|---|---|---|---|---|
| Example 16 | E16 | Titanium isopropoxide | 0.42 g | Quinaldic acid | 0.26 g | n-Propyltrimethoxy silane | 0.24 g | 15.1 g |
| Comparative Example 5 | C5 | Titanium isopropoxide | 0.82 g | — | — | n-Propyltrimethoxy silane | 0.46 g | 15.0 g |

Examples 17 to 23

The charging member E1 was similarly evaluated for the presence or absence of abnormal discharge by increasing the transfer voltage from 1,856 V. As a result, the abnormal discharge was not observed until the transfer voltage was increased to 1,976 V. In addition, the charging members E6 and E12 to E16 were similarly evaluated. Table 8-4 summarizes the results.

The foregoing results of the evaluation show that the charging member having the surface layer of the present invention can significantly suppress abnormal discharge. The charging member having the surface layer of the present invention facilitates the discharge of an electron because a compound having a specific structure coordinates to a metal atom. Probably as a result of the foregoing, a discharge start voltage reduces, an electric field between a photosensitive member and the charging member can be made proper, and a discharge charge quantity is suppressed, and hence local and strong discharge (abnormal discharge) is suppressed.

In addition, the results show that when condensation is advanced by adding water, the local and strong discharge (abnormal discharge) is suppressed in an additionally effective manner. This is probably because of the following reason: when the condensation progresses to additionally shallow the energy level of the highest occupied molecular orbital (HOMO) of a polymetalloxane, an electron is easily discharged, and hence the local and strong discharge (abnormal discharge) is suppressed.

Examples 24 to 28

0.84 Gram of o-anisic acid and 98.4 g of ethanol were weighed in a 100-mL container made of glass, and were stirred to prepare an o-anisic acid/ethanol solution. 0.78 Gram of titanium isopropoxide was added to the prepared o-anisic acid/ethanol solution, and the mixture was stirred to provide a coating liquid E17.

In addition, a coating liquid E18, a coating liquid E19, a coating liquid E20, and a coating liquid E21 were prepared by the same method as the foregoing except that 2,3-dimethoxybenzoic acid, 2,4-dimethoxybenzoic acid, 2,5-dimethoxybenzoic acid, and 2,6-dimethoxybenzoic acid were used instead of o-anisic acid, respectively. Table 7-4 collectively shows the weights.

Charging members E16 to E20 were produced and subjected to the evaluation in the same manner as in Example 1 except that the coating liquids E17 to E21 were used, respectively. Table 8-5 shows the results of the evaluation.

TABLE 7-4

|  | Coating liquid | Metal alkoxide | | Compound for ligand | | Ethanol |
|---|---|---|---|---|---|---|
| Example 24 | E17 | Titanium isopropoxide | 0.78 g | o-Anisic acid | 0.84 g | 98.4 g |
| Example 25 | E18 | Titanium isopropoxide | 0.66 g | 2,3-Dimethoxybenzoic acid | 0.86 g | 98.6 g |
| Example 26 | E19 | Titanium isopropoxide | 0.66 g | 2,4-Dimethoxybenzoic acid | 0.85 g | 98.5 g |
| Example 27 | E20 | Titanium isopropoxide | 0.67 g | 2,5-Dimethoxybenzoic acid | 0.86 g | 98.5 g |
| Example 28 | E21 | Titanium isopropoxide | 0.67 g | 2,6-Dimethoxybenzoic acid | 0.86 g | 98.5 g |

TABLE 8-1

|  | Charging member | Metal alkoxide | Compound for ligand | Metal alkoxide/Compound for ligand mol/mol | Ion-exchanged water | Observation of abnormal discharge |
|---|---|---|---|---|---|---|
| Example 1 | Charging member E1 | Titanium isopropoxide | Guaiacol | 1/1 | — | A |
| Example 2 | Charging member E2 | Titanium isopropoxide | Guaiacol | 1/2 | — | A |
| Example 3 | Charging member E3 | Titanium isopropoxide | 2-Acetylpyrrole | 1/1 | — | A |
| Example 4 | Charging member E4 | Titanium isopropoxide | 2-(Methylthio)phenol | 1/1 | — | A |
| Example 5 | Charging member E5 | Titanium isopropoxide | Methyl 3-hydroxy-2-naphthoate | 1/1 | — | A |

TABLE 8-1-continued

| | Charging member | Metal alkoxide | Compound for ligand | Metal alkoxide/Compound for ligand mol/mol | Ion-exchanged water | Observation of abnormal discharge |
|---|---|---|---|---|---|---|
| Example 6 | Charging member E6 | Titanium isopropoxide | Quinaldic acid | 1/1 | — | A |
| Example 7 | Charging member E7 | Titanium isopropoxide | N,N-Dimethylglycine | 1/1 | — | A |
| Example 8 | Charging member E8 | Pentamethylcyclopentadienyl titanium trimethoxide | — | — | — | A |
| Example 9 | Charging member E9 | Titanium isopropoxide | 2-Amino-p-cresol | 1/1 | — | A |
| Comparative Example 1 | Charging member C1 | Titanium isopropoxide | — | — | — | B |

TABLE 8-2

| | Charging member | Metal alkoxide | Compound for ligand | Metal alkoxide/Compound for ligand mol/mol | Ion-exchanged water | Observation of abnormal discharge |
|---|---|---|---|---|---|---|
| Example 10 | Charging member E10 | Aluminum sec-butoxide | Guaiacol | 1/1 | — | A |
| Comparative Example 2 | Charging member C2 | Aluminum sec-butoxide | — | — | — | B |
| Example 11 | Charging member E11 | Zirconium(IV) propoxide | Guaiacol | 1/1 | — | A |
| Comparative Example 3 | Charging member C3 | Zirconium(IV) propoxide | — | — | — | B |
| Example 12 | Charging member E12 | Tungsten(V) ethoxide | Guaiacol | 1/1 | — | A |
| Example 13 | Charging member E13 | Tungsten(V) ethoxide | Guaiacol | 1/2 | — | A |
| Example 14 | Charging member E14 | Tungsten(V) ethoxide | Guaiacol | 1/3 | — | A |
| Comparative Example 4 | Charging member C4 | Tungsten(V) ethoxide | — | — | — | B |

TABLE 8-3

| | Charging member | Metal alkoxide | Compound for ligand | Metal alkoxide/Compound for ligand mol/mol | Ti/Si mol/mol | Ion-exchanged water | Observation of abnormal discharge |
|---|---|---|---|---|---|---|---|
| Example 15 | Charging member E15 | Titanium isopropoxide | Quinaldic acid | 1/1 | — | Added | A |
| Example 16 | Charging member E16 | Titanium isopropoxide | Quinaldic acid | 1/1 | 1/1 | Added | A |
| Comparative Example 5 | Charging member C5 | Titanium isopropoxide | — | — | 1/1 | Added | B |

TABLE 8-4

| Example | Charging member | Transfer voltage at which abnormal discharge occurs |
|---|---|---|
| Example 17 | Charging member E1 | 1,976 V |
| Example 18 | Charging member E6 | 2,096 V |
| Example 19 | Charging member E12 | 2,096 V |
| Example 20 | Charging member E13 | 2,335 V |
| Example 21 | Charging member E14 | 2,335 V |
| Example 22 | Charging member E15 | 2,814 V |
| Example 23 | Charging member E16 | 2,335 V |

TABLE 8-5

| | Charging member | Metal alkoxide | Compound for ligand | Metal alkoxide/Compound for ligand mol/mol | Ion-exchanged water | Observation of abnormal discharge |
|---|---|---|---|---|---|---|
| Example 24 | Charging member E17 | Titanium isopropoxide | o-Anisic acid | 1/2 | — | A |
| Example 25 | Charging member E18 | Titanium isopropoxide | 2,3-Dimethoxybenzoic acid | 1/2 | — | A |
| Example 26 | Charging member E19 | Titanium isopropoxide | 2,4-Dimethoxybenzoic acid | 1/2 | — | A |
| Example 27 | Charging member E20 | Titanium isopropoxide | 2,5-Dimethoxybenzoic acid | 1/2 | — | A |
| Example 28 | Charging member E21 | Titanium isopropoxide | 2,6-Dimethoxybenzoic acid | 1/2 | — | A |

TABLE 9

| Name | CAS No. | Manufacturer | Remark |
|---|---|---|---|
| 2-Butanol | 78-92-2 | KANTO CHEMICAL CO., INC. | Special grade |
| Ethanol | 64-17-5 | KISHIDA CHEMICAL Co., Ltd. | Special grade |
| Ion-exchanged water | | KYOEI PHARMACEUTICAL CO., LTD. | Ion exchange + distillation |
| Titanium isopropoxide | 546-68-9 | KISHIDA CHEMICAL Co., Ltd. | |
| Pentamethylcyclopentadienyl titanium trimethoxide | 123927-75-3 | Gelest | |
| Aluminum sec-butoxide | 2269-22-9 | KISHIDA CHEMICAL Co., Ltd. | |
| Zirconium(IV) propoxide | 23519-77-9 | KISHIDA CHEMICAL Co., Ltd. | 70 wt % n-propanol solution |
| Tungsten(V) ethoxide | 26143-11-3 | Gelest | |
| 2-Acetylpyrrole | 1072-83-9 | Tokyo Chemical Industry Co., Ltd. | |
| Quinaldic acid | 93-10-7 | Tokyo Chemical Industry Co., Ltd. | |
| Guaiacol | 90-5-1 | Tokyo Chemical Industry Co., Ltd. | |
| 2-(Methylthio)phenol | 1073-29-6 | Tokyo Chemical Industry Co., Ltd. | |
| Methyl 3-hydroxy-2-naphthoate | 883-99-8 | Tokyo Chemical Industry Co., Ltd. | |
| N,N-Dimethylglycine | 1118-68-9 | Tokyo Chemical Industry Co., Ltd. | |
| 2-Amino-p-cresol | 95-84-1 | Tokyo Chemical Industry Co., Ltd. | |
| o-Anisic acid | 579-75-9 | Tokyo Chemical Industry Co., Ltd. | |
| 2,3-Dimethoxybenzoic acid | 1521-38-6 | Tokyo Chemical Industry Co., Ltd. | |
| 2,4-Dimethoxybenzoic acid | 91-52-1 | Tokyo Chemical Industry Co., Ltd. | |
| 2,5-Dimethoxybenzoic acid | 2785-98-0 | Tokyo Chemical Industry Co., Ltd. | |
| 2,6-Dimethoxybenzoic acid | 1466-76-8 | Tokyo Chemical Industry Co., Ltd. | |
| Trimethoxy(n-propyl)silane | 1067-25-0 | Tokyo Chemical Industry Co., Ltd. | |

TABLE 10

Example 1

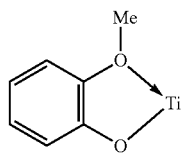

Example 2

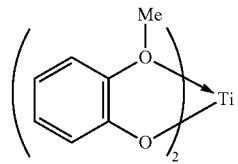

Example 3

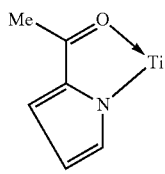

TABLE 10-continued

Example 4

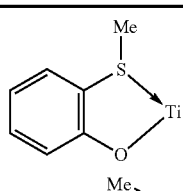

Example 5

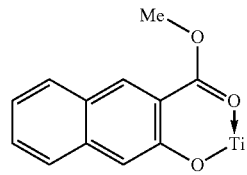

Example 6

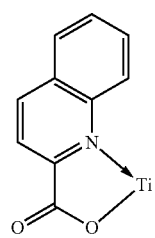

TABLE 10-continued

| Example 7 | 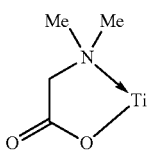 |
| Example 8 | 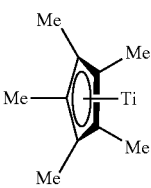 |
| Example 9 | 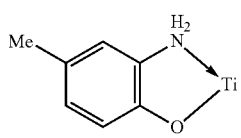 |
| Example 10 | 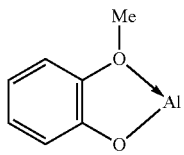 |
| Example 11 | 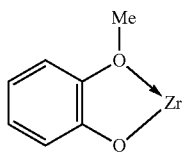 |
| Example 12 | 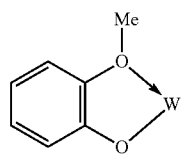 |
| Example 13 | 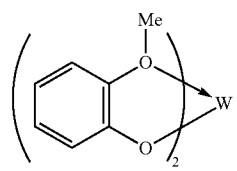 |
| Example 14 | 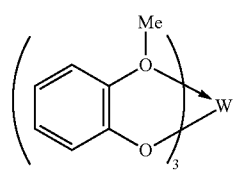 |
| Example 15 | 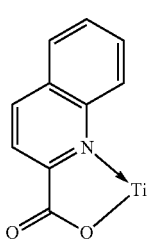 |

TABLE 10-continued

| Example 16 | 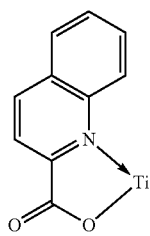 |
| Example 24 | 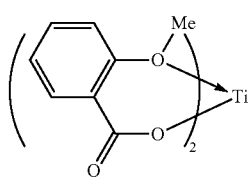 |
| Example 25 | 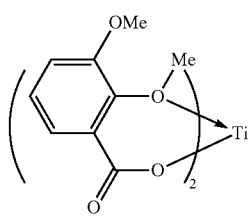 |
| Example 26 | 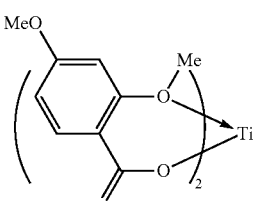 |
| Example 27 | 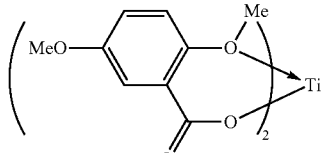 |
| Example 28 | 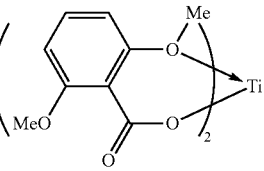 |

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-272398, filed Dec. 27, 2013, which is hereby incorporated by reference herein in its entirety.

What is claimed is:
1. A charging member, comprising:
a support; and
a surface layer on the support, wherein
the surface layer contains a compound represented by formulae (a) or (a1):

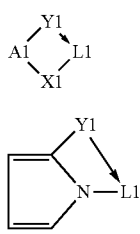
(a)

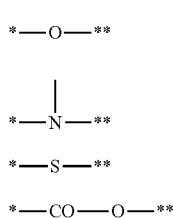
(a1)

where L1 represents a polymetalloxane having a structural unit represented by M1O$_{n/2}$;

n represents an integer of 1 to p when a valence of a metal atom M1 is p;

M1 represents at least one metal atom selected from the group consisting of Ti, Zr, Hf, V, Nb, Ta, W, Al, Ga, In, and Ge;

X1 represents any one of structures represented by formulae (1) to (4):

*—O—** (1)

*—N—** (2)

*—S—** (3)

*—CO—O—** (4)

where * represents a bonding site with A1 and ** represents a bonding site with M1 in L1;

Y1 represents a group having a site that coordinates to M1 in L1; and (i) when X1 represents a structure represented by formula (1), A1 represents an atomic group containing an aromatic ring needed for forming a four- to eight-membered ring together with M1, X1, and Y1, and one constituent carbon atom of the aromatic ring is bonded to an oxygen atom of X1, and (ii) when X1 represents a structure represented by any one of formulae (2) to (4), A1 represents a bond or atomic group needed for forming a four- to eight-membered ring together with M1, X1, and Y1.

2. A charging member according to claim 1, wherein Y1 represents a hydroxy group, an alkoxy group, a substituted or unsubstituted aryloxy group, a carbonyl group, an alkylthio group, a substituted or unsubstituted arylthio group, a thiocarbonyl group, a substituted or unsubstituted amino group, a substituted or unsubstituted imino group, a group having a substituted or unsubstituted aliphatic heterocyclic skeleton, or a group having a substituted or unsubstituted aromatic heterocyclic skeleton.

3. A charging member according to claim 1, wherein A1 represents an atomic group containing an aromatic ring selected from the group consisting of a substituted or unsubstituted benzene ring, a substituted or unsubstituted naphthalene ring, a substituted or unsubstituted pyrrole ring, a substituted or unsubstituted thiophene ring, a substituted or unsubstituted furan ring, a substituted or unsubstituted pyridine ring, a substituted or unsubstituted indole ring, a substituted or unsubstituted benzothiophene ring, a substituted or unsubstituted benzofuran ring, a substituted or unsubstituted quinoline ring, and a substituted or unsubstituted isoquinoline ring when X1 represents a structure represented by formula (1).

4. A charging member according to claim 1, wherein when X1 represents a structure represented by any one of formulae (2) to (4), A1 represents a bond, an alkylene group, or an atomic group containing an aromatic ring selected from the group consisting of a substituted or unsubstituted benzene ring, a substituted or unsubstituted naphthalene ring, a substituted or unsubstituted pyrrole ring, a substituted or unsubstituted thiophene ring, a substituted or unsubstituted furan ring, a substituted or unsubstituted pyridine ring, a substituted or unsubstituted indole ring, a substituted or unsubstituted benzothiophene ring, a substituted or unsubstituted benzofuran ring, a substituted or unsubstituted quinoline ring, and a substituted or unsubstituted isoquinoline ring.

5. A charging member according to claim 1, wherein a ring formed by A1, M1, X1, and Y1 comprises a five-membered ring or a six-membered ring.

6. A charging member according to claim 1, wherein A1 represents a structure represented by formula (A1-1) or (A1-2):

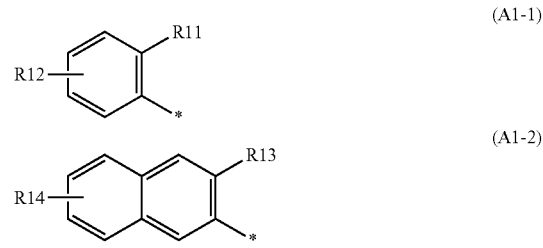

where R11 and R13 each represent a single bond or methylene group bonded to Y1, R12 and R14 each represent a hydrogen atom, a methoxy group, or an ethoxy group, and * represents a bonding site with X1;

X1 represents a structure represented by formula (X1-1) or (X1-2):

*—O—** (X1-1)

*—CO—O—** (X1-2)

where * represents a bonding site with A1 and ** represents a bonding site with M1; and Y1 represents a methoxy group, an ethoxy group, a formyl group, a methylcarbonyl group, an ethylcarbonyl group, a methoxycarbonyl group, an ethoxycarbonyl group, a dimethylamide group, a diethylamide group, a methylethylamide group, a methylthio group, an ethylthio group, a thiocarbonyl group, a dimethylamino group, a diethylamino group, an ethylmethylamino group, an unsubstituted imino group, a methylimino group, an ethylimino group, a group having a pyridine skeleton, a group having a quinoline skeleton, or a group having an isoquinoline skeleton.

7. A charging member according to claim 1, wherein A1 represents a bond, a methylene group, an ethylene group, or a trimethylene group;

X1 represents a structure represented by any one of formulae (X1-3), (X1-4), (X1-6) or (X1-7)

*—NCH$_3$—** (X1-3)

*—NH—** (X1-4)

*—S—** (X1-6)

*—CO—O—** (X1-7)

where * represents a bonding site with A1 and ** represents a bonding site with M1; and Y1 represents a methoxy group, an ethoxy group, a formyl group, a methylcarbonyl group, an ethylcarbonyl group, a methoxycarbonyl group, an ethoxycarbonyl group, a dimethylamide group, a diethylamide group, a methylethylamide group, a methylthio group, an ethylthio group, a thiocarbonyl group, a dimethylamino group, a diethylamino group, an ethylmethylamino group, an unsubstituted imino group, a methylimino group, an ethylimino group, a group having a pyridine skeleton, a group having a quinoline skeleton, or a group having an isoquinoline skeleton.

8. A charging member according to claim 1, wherein the polymetalloxane has a structural unit represented by $SiO_{r/2}$ where r represents an integer of 1 to 4.

9. A process cartridge, comprising:
an electrophotographic photosensitive member; and
a charging member placed to be capable of charging a surface of the electrophotographic photosensitive member,
the process cartridge being removably mounted onto a main body of an electrophotographic apparatus, wherein
the charging member comprises the charging member according to claim 1.

10. An electrophotographic apparatus, comprising:
an electrophotographic photosensitive member; and
a charging member placed to be capable of charging a surface of the electrophotographic photosensitive member, wherein
the charging member comprises the charging member according to claim 1.

* * * * *